(12) United States Patent
Cyr et al.

(10) Patent No.: US 6,902,718 B2
(45) Date of Patent: *Jun. 7, 2005

(54) STABILIZATION OF RADIOPHARMACEUTICAL COMPOSITIONS USING HYDROPHILIC THIOETHERS

(75) Inventors: John E. Cyr, Bedford, NH (US); Daniel A. Pearson, Bedford, NH (US)

(73) Assignee: Diatide, Inc., Montville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/131,543

(22) Filed: Apr. 24, 2002

(65) Prior Publication Data

US 2003/0072709 A1 Apr. 17, 2003

Related U.S. Application Data

(63) Continuation-in-part of application No. PCT/US01/50423, filed on Oct. 24, 2001, and a continuation-in-part of application No. 09/694,992, filed on Oct. 24, 2000, now abandoned.

(51) Int. Cl.[7] .................. A61K 51/00; A61M 36/14
(52) U.S. Cl. .................. 424/1.45; 424/1.11; 424/1.65; 424/9.1; 424/1.69; 424/1.73; 424/1.49; 206/223
(58) Field of Search .................. 424/1.11, 1.49, 424/1.65, 1.69, 9.1, 1.37, 1.45, 1.53, 1.73; 206/223, 569, 570; 534/10–16; 530/300, 301–338; 549/1, 13, 23, 200

(56) References Cited

U.S. PATENT DOCUMENTS

| | | | |
|---|---|---|---|
| 4,048,296 A | 9/1977 | Wolfangel | |
| 4,062,933 A | 12/1977 | Wolfangel | |
| 4,229,427 A | 10/1980 | Whitehouse | |
| 4,232,000 A | 11/1980 | Fawzi | |
| 4,233,284 A | 11/1980 | Fawzi | |
| 4,451,451 A | 5/1984 | Rimmer | |
| 4,497,744 A | 2/1985 | Fawzi | |
| 4,857,299 A | 8/1989 | Chia et al. | |
| 5,272,135 A | 12/1993 | Takruri | |
| 5,358,708 A | 10/1994 | Patel | |
| 5,384,113 A | 1/1995 | Deutsch et al. | |
| 5,393,512 A | 2/1995 | Vanderheyden et al. | |
| 5,849,261 A | * 12/1998 | Dean et al. | 424/1.69 |
| 6,030,950 A | 2/2000 | Ohlenschläger | |
| 2003/0103895 A1 | * 6/2003 | Cyr et al. | 424/1.11 |

FOREIGN PATENT DOCUMENTS

| | | | |
|---|---|---|---|
| DE | 3722647 A1 | 1/1989 | |
| WO | WO 95/01188 | 1/1995 | ......... A61K/49/02 |
| WO | WO 00/61195 | 10/2000 | ......... A61K/51/04 |

OTHER PUBLICATIONS

Pearson et al (1996), J. Med. Chem., 39, 1361–1371.*

* cited by examiner

*Primary Examiner*—Dameron L. Jones
(74) *Attorney, Agent, or Firm*—Fish & Richardson P.C.

(57) ABSTRACT

Radiopharmaceutical compositions which are stabilized by addition of a hydrophilic thioether.

23 Claims, No Drawings

STABILIZATION OF RADIOPHARMACEUTICAL COMPOSITIONS USING HYDROPHILIC THIOETHERS

CROSS-REFERENCE TO RELATED APPLICATION

This application is a continuation-in-part of U.S. application Ser. No. 09/694,992 filed on 24 Oct. 2000 now abandoned and a continuation-in-part of International Application No. PCT/US 01/50423 filed on 24 Oct. 2001.

This application also is related to commonly assigned U.S. patent application Ser. No. 09/695,360 "Stabilization of Radiopharmaceutical Compositions Using Hydrophilic 6-hydroxy Chromans" and to commonly assigned U.S. patent application Ser. No. 695,494 "Stabilization of Radiopharmaceutical Compositions Using Hydrophilic Thioethers and Hydrophilic 6-hydroxy Chromans" both of which were filed on 24 Oct. 2000.

BACKGROUND OF THE INVENTION

The present invention relates to novel stabilizers of radiopharmaceutical compositions used for diagnosis and therapy. In particular, the invention relates to use of a hydrophilic thioether, to increase the shelf-life of diagnostic and therapeutic radiopharmaceuticals.

A number of radionuclides are routinely employed in nuclear medicine, both as diagnostic agents and as therapeutics. For example, $^{99m}Tc$, $^{111}In$, $^{18}F$, and $^{201}Tl$ are employed as diagnostic imaging agents, and $^{131}I$, $^{32}P$, $^{89}Sr$, and $^{153}Sm$ are in therapeutic use. In addition, nuclides such as $^{186}Re$, $^{188}Re$, $^{212}Bi$, $^{213}Bi$, $^{90}Y$, $^{67}Cu$, $^{192}Ir$, $^{165}Dy$, and $^{117m}Sn$ have been proposed as potential therapeutic agents. Such radionuclides are administered in the form of radiopharmaceutical compositions, which generally include a chelator for the nuclide. Radiopharmaceuticals may additionally include a targeting molecule such as a monoclonal antibody, an antibody fragment, or a receptor ligand. The availability of radiopharmaceuticals has significantly advanced diagnosis and treatment of a variety of diseases.

Chemical decomposition may limit a radiopharmaceutical's shelf life by decreasing the radiochemical purity of the agent over time. For example, a radiopharmaceutical containing $^{99m}Tc$, $^{186}Re$, or $^{188}Re$ may be susceptible to oxidation of the nuclide itself. In addition, the radiation emitted from a radionuclide can break chemical bonds of other components of the composition, thus causing autoradiolysis. Autoradiolysis is a particular problem when the radiopharmaceutical contains higher energy nuclides, such as β-emitters (e.g., $^{186}Re$, $^{188}Re$, $^{90}Y$, $^{131}I$) and α-emitters (e.g., $^{213}Bi$, $^{212}Bi$, $^{211}At$, $^{225}Ac$, $^{223}Ra$).

Thus many radiopharmaceuticals require stabilizers to maximize shelf life. Such stabilizers must be non-toxic and must be able to maintain the product's radiochemical purity for an acceptable shelf-life as well as during use. In addition, an acceptable radiopharmaceutical stabilizer must not interfere with delivery of the radionuclide to the target site.

Methods for stabilizing radiopharmaceuticals by adding gentisates are disclosed, for example, in U.S. Pat. Nos. 4,232,000; 4,233,284; 4,497,744; 5,384,113. Stabilization of radiopharmaceuticals using ascorbic acid is disclosed in U.S. Pat. Nos. 5,393,512 and 5,011,676, in WO 97/28181 and in WO 98/33531. Hydroquinone stabilizers of radiopharmaceuticals is disclosed in U.S. Pat. No. 4,229,427. Other compounds such as reductic acid, erythorbic acid, p-aminobenzoic acid, 4-hydroxybenzoic acid, nicotinic acid, nicotinamide, 2,5-dihydroxy-1,4-benzenedisulfonic acid, tartaric acid, inositol, and the like, have also been used to stabilize radiopharmaceutical compositions.

U.S. Pat. No. 5,384,113 discloses a method of preventing autoradiolysis of peptides radiolabeled with $^{111}In$ using gentisic acid or gentisyl alcohol. In addition to preventing autoradiolysis of peptides by $^{111}In$, the method of U.S. Pat. No. 5,384,113 is proposed to prevent autoradiolysis of peptides by $^{67}Ga$, $^{169}Yb$, $^{125}I$, $^{123}I$, and $^{201}Tl$. Two radiolabelled peptides, $^{111}In$-DTPA-octreotide and 123I-LHRH, were tested for autoradiolysis prevention. A monoclonal antibody, NR-Lu-10, labeled with $^{186}Re$ was also specifically exemplified.

As indicated in Example 1, infra, the present inventors have found that that when added as a component in radiopharmaceutical kit formulations, gentisic acid decreases the radiochemical purity of some $^{99m}Tc$-labelled peptides, and thus is not useful as a stabilizer of some radiolabeled peptides. A need exists, therefore, for additional stabilizers of radiopharmaceuticals. A particular need exists for stabilizers of radiopharmaceuticals containing less than 70 amino acids linked by peptide bonds.

Methionine residues in proteins and polypeptides are known to oxidize to methionine sulfoxide. U.S. Pat. No. 5,272,135 discloses a method of inhibiting oxidation of a liquid or semi-liquid composition of a polypeptide containing at least one methionine residue by adding between 0.01% w/v to 0.3% w/v methionine to the composition. U.S. Pat. No. 5,272,135 teaches that the method disclosed therein is effective with a variety of polypeptides, including epidermal growth factor, insulin-like growth factor I, nerve growth factor, transforming growth factor alpha precursor, transforming growth factor beta precursor, transforming growth factor beta, fibroblast growth factor, vaccinia growth factor, platelet derived growth factor, or methionine containing biologically active fragments or precursors of such growth factors. However, the data presented in U.S. Pat. No. 5,272,135 are limited to addition of methionine to inhibit oxidation of methionine residues present in epidermal growth factor. Lam, et al. (1997) *J. Pharm. Sci.* 86, 1250–1255 disclose the use of methionine to stabilize the recombinant humanized monoclonal antibody rhuMAb HER2 in liquid formulations to prevent oxidation of methionine residues.

U.S. Pat. No. 5,358,708 discloses a method for increasing the storage stability of an aqueous formulation of granulocyte-macrophage colony stimulating factor or an interleukin by addition of a stabilizing amount of methionine, histidine, or mixtures thereof. U.S. Pat. No. 5,358,708 also discloses that chemical differences among proteins causes different proteins to become inactivated during storage at different rates and under different conditions. U.S. Pat. No. 5,358,708 further discloses that the storage-prolonging effects of methionine and histidine are not equivalent with different proteins, and that mixtures of amino acids exhibit different effects as the ratio varies, as the identity of the protein is changed, and/or as concentrations are altered.

WO 97/14430 discloses use of hydrophilic thioethers as antioxidants to prolong storage stability of aqueous formulations of proteins and peptides. The only data presented in WO 97/14430 relate to insulin-like growth factor I, a 70-amino acid peptide containing three disulfide bonds. WO 97/14430 further discloses that common antioxidants such as ascorbic acid, sodium thiosulfate, glutathione, or sodium bisulfite increased oxidation of IGF-1 or even precipitated the protein.

SUMMARY OF THE INVENTION

It has now been surprisingly found that the radiolabelling efficiency and shelf-life of peptide and non-peptide radiopharmaceutical compositions may be significantly increased by addition of a stabilizing amount of a hydrophilic thioether.

In one embodiment, the invention provides a composition comprising a radiopharmaceutical precursor and a stabilizing amount of a hydrophilic thioether.

In another embodiment, the invention provides a method of stabilizing a radiopharmaceutical comprising the steps of:

a) combining a precursor of said radiopharmaceutical with a stabilizing amount of a hydrophilic thioether in a container; and b) adding a radionuclide to the container.

In a further embodiment, the invention provides a kit comprising a sealed vial containing a predetermined quantity of a radiopharmaceutical precursor and a stabilizing amount of a hydrophilic thioether.

DETAILED DESCRIPTION OF THE INVENTION

The patent and scientific literature referenced herein establish the knowledge available to those with skill in the art. The issued U.S. patents are hereby incorporated by reference.

As defined herein, a "radiopharmaceutical" or "radiopharmaceutical composition" comprises a radionuclide, a chelator, and optionally a targeting moiety or domain.

In accordance with the invention, a "precursor" of a radiopharmaceutical is defined as comprising an unlabelled, that is, non-radioactive, reagent which may be a chelator or a chelator covalently linked to a targeting moiety or domain.

A "targeting moiety or domain" as defined herein as a moiety or domain capable of binding specifically to a site within a mammalian body such as a receptor on a cell surface. Targeting moieties or domains within the scope of the present invention include but are not limited to antibodies, antibody fragments such as Fab or F(ab)'$_2$ fragments, epitope binding complementarity determining regions derived from antibodies, peptides, growth factors or receptor binding fragments thereof, hormones, steroids, receptor binding nucleic acids, receptor binding carbohydrates including monosaccharides, disaccharides, and oligosaccharides, receptor-binding lipids, benzodiazepines, receptor binding antibiotics, and the like.

A "stabilizing amount" is defined herein as that amount of hydrophilic thioether, sufficient to maintain the radiochemical purity, as measured by known methods such as those disclosed in the examples below, of a radiopharmaceutical composition relative to that of the radiopharmaceutical composition without the additive for at least 3 hours. Preferably, a clinically acceptable radiochemical purity for a radiopharmaceutical is at least 80% of the labelled undegraded radiopharmaceutical. More preferably, a clinically acceptable radiochemical purity for a radiopharmaceutical is at least 85% of the labelled undegraded radiopharmaceutical. Most preferably, a clinically acceptable radiochemical purity for a radiopharmaceutical is at least 90% of the labelled undegraded radiopharmaceutical.

Preferably, a stabilizing amount of hydrophilic thioether is in the range of about 0.1% (w/v) to about 1.5% (w/v). More preferably, a stabilizing amount of hydrophilic thioether is in the range of about 0.4% (w/v) to about 1.0% (w/v). More preferably, a stabilizing amount of hydrophilic thioether is in the range of about 0.5% (w/v) to about 1.0% (w/v).

A "hydrophilic thioether" is defined in accordance with the present invention as a compound having the general structure:

$$R\text{—}S\text{—}CH_2C(R^1R^2R^3)$$

wherein:

R is $C_1$ to $C_4$ alkyl or a $C_1$ to $C_4$ alkyl containing at least one hydrophilic group selected from —COOH, —NH$_2$, —NHR$^4$, —NR$^4_2$, —OH, —SO$_2$R$^4$, —SOR$^4$, —SO$_3$H, —CONH$_2$, —CONHR$^4$, —CONR$^4_2$, —COOR$^4$, —OR$^4$, —SR$^4$, —NO$_2$, —SO$_2$NH$_2$, —SO$_2$NHR$^4$, and —SO$_2$NR$^4_2$; with the proviso that, when R is methyl, the hydrophilic group is not NH$_2$, NHR$^4$, NR$^4_2$ or OH;

R$^1$, R$^2$, and R$^3$ are each independently selected from the group consisting of H, —COOH, —NH$_2$, —NHR$^4$, —NR$^4_2$, —OH, —SO$_2$R$^4$, —SOR$^4$, —SO$_3$H, —CONH$_2$, —CONHR$^4$, —CONR$^4_2$, —COOR$^4$, —OR$^4$, —SR$^4$, —NO$_2$, —SO$_2$NH$_2$, —SO$_2$NHR$^4$, —SO$_2$NR$^4_2$, $C_1$ to $C_4$ alkyl, and a $C_1$ to $C_3$ alkyl containing at least one hydrophilic group selected from —COOH, —NH$_2$, —NHR$^4$, —NR$_2$, —OH, —SO$_2$; —SO$_3$R$^4$, —SO$_3$H, —CONH$_2$, —CONHR$^4$, —CONR$^4_2$, —COOR$^4$, —OR$^4$, —SR$^4$, —NO$_2$, —SO$_2$NH$_2$, —SO$_2$NHR$^4$, and —SO$^4_2$, with the proviso that only one of R$^1$, R$^2$, and R$^3$ is —NH$_2$, NHR$^4$, NR$^4_2$ or OH; and R$^4$ is selected from the group consisting of $C_1$ to $C_3$ alkyl; and with the further proviso that the hydrophilic thioether comprise at least one of said hydrophilic groups.

Specific hydrophilic thioethers of the present invention include D-methionine, L-methionine, D-ethionine, L-ethionine, 3-methylthio-1,2-propanediol, methyl-3-(methylthio)propionate, 2-(ethylthio)ethylamine.HCl, 2-(methylthio)-ethanol, buthionine, S-methyl-L-cysteine, S-methyl-D-cysteine, D-methioninol, L-methioninol, and the like. Preferably, the hydrophilic thioether used in the compositions of the invention is methioninol, 2-(ethylthio)-ethylamine.HCl, 3-methythio-1,2-propanediol, or methionine. More preferably, the hydrophilic thioether used in the compositions of the invention is 2-(ethylthio)-ethylamine.HCl or methionine. Most preferably, the hydrophilic thioether used in the compositions of the invention is L-methionine.

Any radiopharmaceutical may be stabilized by addition of a hydrophilic thioether, as taught herein. Ligand-type radiopharmaceuticals which do not comprise a targeting moiety or domain, such as Tc 99m MAG3 (TechnoScan®, Mallinkrodt Medical, Inc., St. Louis, Mo., U.S.A.), may be stabilized in accordance with the present invention. In addition, radiopharmaceuticals comprising any kind of targeting moiety or domain may be stabilized in accordance with the present invention.

Recently a new class of radiopharmaceuticals has been developed which target a radiolabel to a particular tissue, disease site, or organ through a small receptor-specific molecule, which may be a peptide, a β-glucan, a benzodiazepine, or other small molecule. Such radiopharmaceuticals are disclosed and claimed, for example, in commonly assigned U.S. Pat. Nos. 5,508,020; 5,225,180; 5,405,597; 5,443,815; 5,552,525; 5,561,220; 5,620,675; 5,645,815; 5,654,272; 5,681,541; 5,711,931; 5,714,579; 5,716,596; 5,736,122; 5,770,179; 5,783,170; 5,788,960; 5,807,537; 5,807,538; 5,811,394; 5,814,297; 5,814,298; 5,814,299; 5,820,845; 5,820,846; 5,830,856; 5,833,942; 5,843,401; 5,843,403; 5,849,260; 5,849,261; 5,851,509;

5,866,097; 5,871,711; 5,932,189; 5,951,964; 5,955,426; 5,976,496; 5,997,844; 6,007,792; 6,017,509; 6,017,512; 6,028,056; 6,051,206; 6,074,627; 6,086,850; 6,171,178 and; 6,241,960; and in commonly assigned copending U.S. patent application Ser. Nos. 08/236,402; 08/253,973; 08/721,443; and 09/553,494. These new agents comprise a chelator covalently linked to the receptor-specific targeting moiety or domain, and a radiolabel complexed with the chelator. A kit for making one such agent, ACUTECT®, has received approval in the U.S. for scintigraphic imaging of acute deep vein thrombosis. A second kit, NEOTECT®, has been approved in the U.S. for imaging malignant lung tumors. The stabilizers of the present invention are particularly suitable for use with radiopharmaceuticals which comprise chelators covalently linked to peptide, β-glucan, benzodiazepine, or other small targeting molecules as described in the commonly assigned patents and copending applications listed above.

In general, radiopharmaceuticals containing precursors in which a targeting moiety or domain is covalently linked to a monoamine, diamide, single thiol containing chelator such as those disclosed in commonly assigned copending U.S. patent application Ser. No. 08/253,973 and in WO 95/33497 are stabilized using a hydrophilic thioether, a hydrophilic 6-hydroxy-chroman or a mixture of a hydrophilic thioether and a hydrophilic 6-hydroxy-chroman in accordance with this invention. In addition, radiopharmaceuticals containing precursors in which a targeting moiety or domain is covalently linked to a bisamine bisthiol (BAT) chelator such as those disclosed in commonly assigned U.S. Pat. Nos. 5,780,007; 5,776,428; 5,720,934; 5,922,303; 5,965,107; 6,086,849; and 6,093,383 and in WO 93/21962 maybe stabilized in accordance with the present invention.

The stabilizers of the present invention may also be used for radiopharmaceuticals comprising targeting molecules covalently linked to any chelator, such as the diamine monoamide thiol chelators and the triamine thiol chelators described in U.S. Pat. No. 5,688,485 and the triamide thiols disclosed in U.S. Pat. No. 5,091,514.

The stabilizers of the invention are preferably employed to increase the shelf life of radiopharmaceuticals comprising a targeting moiety covalently linked to a peptide metal chelator having a formula

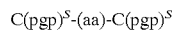

wherein (pgp)$^S$ is H or a thiol protecting group and (aa) is an amino acid. Such chelators are disclosed and claimed in commonly assigned U.S. Pat. Nos. 5,654,272; 5,681,541; 5,788,960; and 5,811,394.

The stabilizers of the invention may also be employed to increase the shelf life of radiopharmaceuticals comprising a targeting moiety covalently linked to a peptide metal chelator having a formula selected from the group consisting of:

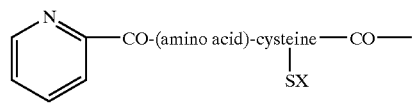

wherein

X is H or a protecting group;

(amino acid) is any amino acid;

and

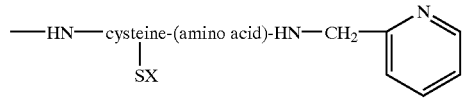

wherein

X is H or a protecting group;

(amino acid) is any amino acid.

Such chelators are disclosed and claimed in commonly assigned U.S. Pat. Nos. 5,720,934; 5,776,428; 5,780,007; 6,086,849 and 6,093,383.

More preferably, the stabilizers of the invention are used to increase the shelf life of radiopharmaceuticals comprising a targeting moiety covalently linked to a peptide metal chelator comprising a single thiol having a formula:

wherein

A is H, HOOC, H$_2$NOC, (peptide)-NHOC, (peptide)-OOC or R"";

B is H, SH, —NHR''', —N(R''')-(peptide), or R"";

X is H, SH, —NHR''', —N(R''')-(peptide) or R"";

Z is H or R"";

R', R", R''' and R"" are independently H or lower straight or branched chain or cyclic alkyl;

n is 0, 1 or 2;

and where B is —NHR''' or —N(R''')-(peptide), X is SH, and n is 1 or 2;

where X is —NHR''' or —N(R''')-(peptide), B is SH, and n is 1 or 2;

where B is H or R"", A is HOOC, H$_2$NOC, (peptide)—NHOC, (peptide)-OOC, X is SH, and n is 0 or 1;

where A is H or R"", then where B is SH, X is —NHR''' or —N(R''')-(peptide) and where X is SH, B is —NHR''' or —N(R''')-(peptide);

where X is H or R"", A is HOOC, H$_2$NOC, (peptide)-NHOC, (peptide)-OOC and B is SH;

where Z is methyl, X is methyl, A is HOOC, H$_2$NOC, (peptide)-NHOC, (peptide)-OOC, B is SH and n is 0.

Such chelators are disclosed and claimed in commonly assigned U.S. Pat. Nos. 5,443,815; 5,807,537; 5,814,297; and 5,866,097.

Specific embodiments of the single thiol containing radiometal chelator stabilized in accordance with the present invention are described and claimed in commonly assigned copending U.S. patent application Ser. No. 08/236,402 and in WO 95/29708, and include chelators having the chemical formula:

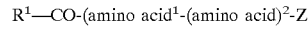

wherein (amino acid)$^1$ and (amino acid)$^2$ are each independently any primary α- or β-amino acid that does not comprise a thiol group, Z is a thiol-containing moiety selected from the group consisting of cysteine, homocysteine, isocysteine, penicillamine, 2-mercaptoethylamine and 3-mercaptopropylamine, and R$^1$ is lower (C$^1$–C$^4$) alkyl, an amino acid, or a peptide comprising 2 to 10 amino acids. When Z is cysteine, homocysteine, isocysteine or penicillamine, the carbonyl group of said moiety is covalently linked to a hydroxyl group, a NR$^3$R$^4$ group, wherein each of $R^3$ and $R^4$ are independently H or lower ($C^1-C^4$) alkyl, an amino acid or a peptide comprising 2 to 10 amino acids.

Alternatively, a single thiol containing radiometal chelator stabilized in accordance with the present invention has a formula:

Y-(amino acid)$^2$-(amino acid)$^1$—NHR$^2$ wherein Y is a thiol-containing moiety that is cysteine, homocysteine, isocysteine, penicillamine, 2-mercaptoacetate or 3-mercaptopropionate, (amino acid)$^1$ and (amino acid)$^2$ are each independently any primary α- or β-amino acid that does not comprise a thiol group, and $R^2$ is H or lower ($C^1-C^4$) alkyl, an amino acid or a peptide comprising 2 to 10 amino acids. When Y is cysteine, homocysteine, isocysteine or penicillamine, the amino group of said moiety is covalently linked to —H, an amino acid or a peptide comprising 2 to 10 amino acids.

Specific embodiments of the single thiol containing radiometal chelator are selected from the group consisting of:

-(amino acid)$^1$-(amino acid)$^2$-A-CZ(B)—{C(R$^1$R$^2$)}$_n$—X},

-A-CZ(B)—{C(R$^1$R$^2$)}$_n$—X}-(amino acid)$^1$-(amino acid)$^2$,

-(a primary α, ω- or β, ω-diamino acid)-(amino acid)$^1$-A-CZ(B)—{C(R$^1$R$^2$)}$_n$—X}, and -A-CZ(B)—{C(R$^1$R$^2$)}$_n$—X}-(amino acid) $^1$-(a primary α,β- or α, ω-diamino acid)

wherein the term "α, ω-diamino acid" represents an amino acid having an amine on the α carbon atom and an amine on the carbon atom most distal from the α carbon atom, the term "β, ω-diamino acid" represents an amino acid having an amine on the β carbon atom and an amine on the carbon atom most distal from the β carbon atom, and (amino acid)$^1$ and (amino acid)$^2$ are each independently any naturally-occurring, modified, substituted or altered α- or β-amino acid not containing a thiol group.

Specific single thiol-containing radiometal chelators stabilized in accordance with the invention have a formula selected from the group consisting of: -Gly-Gly-Cys-, Cys-Gly-Gly-, -(ε-Lys)-Gly-Cys-, (δ-Om)-Gly-Cys-, -(γ-Dab)-Gly-Cys-, -(β-Dap)-Lys-Cys-, and -(γ-Dap)-Gly-Cys-. (In these formulae, ε-Lys represents a lysine residue in which the ε-amino group, rather than the typical α-amino group, is covalently linked to the carboxyl group of the adjacent amino acid to form a peptide bond; δ-Orn represents an ornithine residue in which the δ-amino group, rather than the typical α-amino group, is covalently linked to the carboxyl group of the adjacent amino acid to form a peptide bond; γ-Dab represents a 2,4-diaminobutyric acid residue in which the γ-amino group is covalently linked to the carboxyl group of the adjacent amino acid to form a peptide bond; and β-Dap represents a 2,3-diaminopropionic acid residue in which the β-amino group is covalently linked to the carboxyl group of the adjacent amino acid to form a peptide bond.)

Most preferably, the stabilizers of the invention may be used to increase the shelf life of radiopharmaceuticals comprising a targeting moiety covalently linked to a monoamine, diamide, single thiol metal chelator such as those disclosed and claimed in commonly assigned copending U.S. patent application Ser. No. 08/253,973 and in WO 95/33497, and to increase the shelf life of radiopharmaceuticals comprising a targeting moiety covalently linked to a bisamide bisthiol metal chelator such as those disclosed and claimed in commonly assigned U.S. Pat. Nos. 5,780,007; 5,922,303; 6,086,849; and 6,093,383. Exemplary monoamine, diamide, single thiol chelators stabilized by a mixture of a hydrophilic thioether and a hydrophilic 6-hydroxy chroman have general formulae selected from the group consisting of:

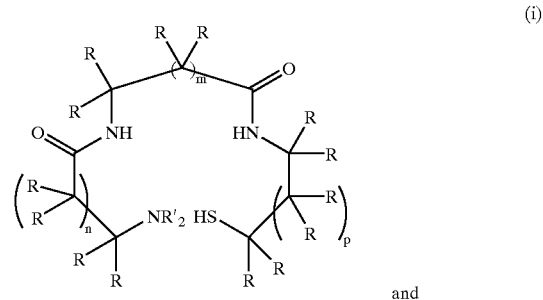

(i)

and

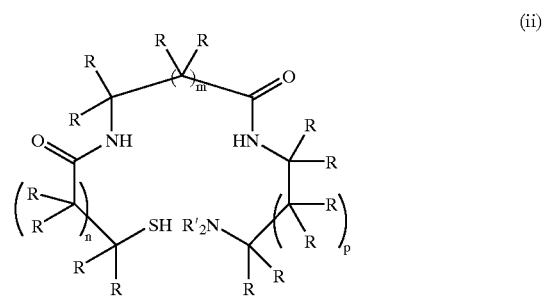

(ii)

wherein n, m and p are each integers that are independently 0 or 1; each R' is independently H, lower alkyl, $C_2-C_4$ hydroxyalkyl, or $C_2-C_4$ alkoxyalkyl, and each R is independently H or R", where R" is a substituted lower alkyl group, an unsubstituted lower alkyl group, or a phenyl not comprising a thiol group, and one R or R' is L, where L is a bivalent linker linking the metal chelator to the targeting moiety and wherein when one R' is L, NR'$_2$ is an amine. In preferred embodiments, L is a $C_1-C_6$ linear alkyl group; a branched chain alkyl group; a cyclic alkyl group; a carboxylic ester; a carboxamide; a sulfonamide; an ether; a thioether; an amine; an alkene; an alkyne; a 1,2-linked, optionally substituted benzene ring; a 1,3-linked, optionally substituted benzene ring; a 1,4-linked, optionally substituted benzene ring; an amino acid, or a peptide of 2 to about 10 amino acids, or combinations thereof. In preferred embodiments, R" is a $C_1-C_6$ linear alkyl group; a branched alkyl group; a cyclic alkyl group; a —C$_q$OC$_r$—, —C$_q$NHC$_r$— or —C$_q$SC$_r$— group, where q and r are integers each independently 1 to 5 wherein the sum of q+r is not greater than 6; a ($C_1-C_6$) alkyl-X, where X is a hydroxyl group; a substituted amine; a guanidine; an amidine; a substituted thiol group; a carboxylic acid; an ester; a phosphate group; a sulfate group; a phenyl group; a phenyl group substituted with a halogen, a hydroxyl, a substituted amine, a guanidine, an amidine, a substituted thiol, an ether, a phosphate group, or a sulfate group; an indole group; a $C_1-C_6$ heterocyclic group containing 1 to 3 nitrogen, oxygen or sulfur atoms; or a combination thereof.

In a specific embodiment, the monoamine, diamide single thiol radiometal chelator stabilized in accordance with the invention may have a formula:

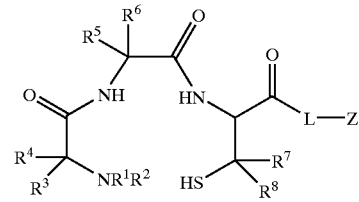

wherein $R^1$ and $R^2$ are each independently H, lower alkyl, $C_2-C_4$ hydroxyalkyl, or $C_2-C_4$ alkoxyalkyl; $R^3$, $R^4$, $R^5$ and $R^6$ are independently H, substituted or unsubstituted lower alkyl or phenyl not comprising a thiol group; $R^7$ and $R^8$ are each independently H, lower alkyl, lower hydroxyalkyl or lower alkoxyalkyl; L is a bivalent linker group and Z is a targeting moiety.

The monoamine, diamide single thiol radiometal chelator stabilized in accordance with the invention may alternatively have a formula:

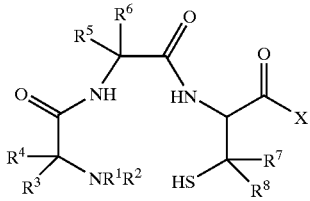

wherein $R^1$ and $R^2$ are each independently H, lower alkyl, $C_2$–$C_4$ hydroxyalkyl, or $C_2$–$C_4$ alkoxyalkyl; $R^3$, $R^4$, $R^5$ and $R^6$ are independently H, substituted lower alkyl, unsubstituted lower alkyl, phenyl, substituted phenyl not comprising a thiol group, and one of $R^3$, $R^4$, $R^5$ or $R^6$ is Z-L-HN(CH$_2$)$_n$—, where L is a bivalent linker, Z is a targeting moiety, and n is an integer from 1 to 6; $R^7$ and $R^8$ are each independently H, lower alkyl, lower hydroxyalkyl, lower alkoxyalkyl; and X is an amino group, a substituted amino group or —NR$^1$—Y, where Y is an amino acid, an amino acid amide, or a peptide comprising from 2 to 10 amino acids.

The monoamine, diamide single thiol radiometal chelator stabilized in accordance with the invention may alternatively have a formula:

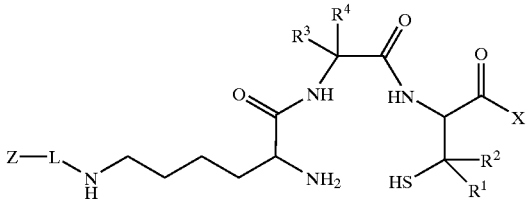

wherein $R^1$ and $R^2$ are each independently H, lower alkyl, lower hydroxyalkyl, or lower alkenylalkyl; $R^3$ and $R^4$ are independently H, substituted or unsubstituted lower alkyl or phenyl not comprising a thiol group; n is an integer from 1 to 6; L is a bivalent linker; and Z is a targeting moiety.

The monoamine, diamide single thiol radiometal chelator stabilized in accordance with the invention may alternatively have a formula:

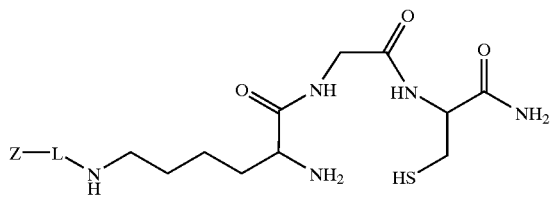

wherein L is a bivalent linker and Z is a targeting moiety.

Bisamide bisthiol metal chelators stabilized in accordance with the present invention preferably have a formula selected from the group consisting of:

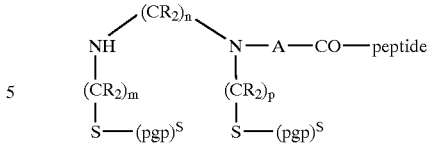

wherein
  each R is independently H, CH$_3$ or C$_2$H$_5$;
  each (pgp)$^S$ is independently a thiol protecting group or H;
  m, n and p are independently 2 or 3;
  A is linear or cyclic lower alkyl, aryl, heterocyclyl, a combination thereof or a substituted derivative thereof, and

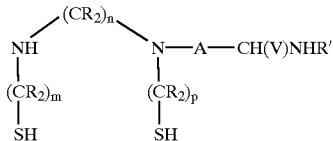

wherein
  each R is independently H, CH$_3$ or C$_2$H$_5$;
  m, n and p are independently 2 or 3;
  A is linear or cyclic lower alkyl, aryl, heterocyclyl, a combination thereof or a substituted derivative thereof,
  V is H or —CO-peptide;
  R' is H or peptide;
  and wherein when V is H, R' is peptide; and when R' is H, V is —CO-peptide.

For example, the stabilizers of the invention may be used to increase the shelf life of radiopharmaceuticals comprising the specific precursors set forth below:
GGCSIPPEVKFNKPFVYLI.amide (SEQ ID NO:1);
GGCSIPPEVKFNKPFVYLI (SEQ ID NO:2);
GGCGLF (SEQ ID NO:3);
RGCSIPPEVKFNXPFVYLI.amide (SEQ ID NO:4);
RGCGHRPLDKKREEAPSLRPAPPPISGGYR.amide (SEQ ID NO:5);
GGCRPKIPQQFFGLM.amide (SEQ ID NO:6),
GGCFVYLI.amide (SEQ ID NO:7);
(acetyl.TKPRGG)$_2$K($\epsilon$-K)GC.amide (SEQ ID NO:13);
F$_D$FYW$_D$KTFT($\epsilon$-K)GC.amide;
acetyl.F$_D$FYW$_D$KTFT($\epsilon$-K)GC.amide;
acetyl.Nal$_D$.Cpa.YW$_D$KTFT($\epsilon$-K)GCKK.amide;
acetyl.F$_D$FYW$_D$KTFTGGG($\epsilon$-K)GC.amide;
acetyl.F$_D$FYW$_D$KTFTGGG($\epsilon$-K)KC.amide;
acetyl.D$_D$F$_D$.Cpa.YW$_D$KTFT($\epsilon$-K)GCKK.amide;
acetyl.D$_D$F$_D$.Cpa.YW$_D$KTC($\epsilon$-K)GCKK.amide;
acetyl.KKKKK.Nal$_D$.Cpa.YW$_D$KTFT($\epsilon$-K)GCKK.amide;
acetyl.Nal$_D$.Cpa.YW$_D$KTFT($\epsilon$-K)GCKK.amide;
acetyl-DDD.Nal$_D$.Cpa.YW$_D$KTFT($\epsilon$-K)GCKK.amide;
acetyl.D$_D$DF$_D$.Cpa.YW$_D$KTFT($\epsilon$-K)GCKK.amide;
(DTPA).F$_D$FYW$_D$KTFT($\epsilon$-K)GC.amide;
(DTPA).Nal$_D$.Cpa.YW$_D$KT.Nal.T($\epsilon$-K)GCKK.amide;
(DTPA).($\epsilon$-K)GCF$_D$FYW$_D$KTFT.amide;
(DTPA).($\epsilon$-K)GCF$_D$.Cpa.YW$_D$KTFT.amide;
(DTPA).F$_D$.Cpa.YW$_D$KTFT($\epsilon$-K)GC.amide;
(DTPA).Nal$_D$.Cpa.YW$_D$KTFT($\epsilon$-K)GC.amide;
(DTPA).Aca.F$_D$.Cpa.YW$_D$KTFT($\epsilon$-K)GC.amide;
(DTPA).Nal$_D$.Cpa.YW$_D$KT.Nal.T($\epsilon$-K)GCKK.amide;

(DTPA).Nal_D.Cpa.YW_DKTFT(ε-K)GCKK.amide;
CH_2CO.FFW_DKTFC(ε-K)GC.amide;
CH_2CO.FFW_DKTFCKKKKK(ε-K)GC.amide;
CH_2CO.FFW_DKTFC(ε-K)KKKKKGC.amide;
AKCGGGF_DFYW_DKTFT.amide;
AKCGGGF_DYW_DKTFT.amide;
DDDD.Nal_D.Cpa.YW_DKTFT(ε-K)GCKKKK.amide;
DDD.Nal_D.Cpa.YW_DKTFT(ε-K)GCKK.amide;
Nal_D.Cpa.YW_DKTFT(ε-K)GCKK.amide;
Trc.Nal_D.Cpa.YW_DKTFT(ε-K)GCKK.amide;
Hca.Nal_D.Cpa.YW_DKTFT(ε-K)GCKK.amide;
(Trc)_2.Nal_D.Cpa.YW_DKTFT(ε-K)GCKK.amide;
KKKK.Nal_D.Cpa.YW_DKTFT(ε-K)GCDDDD.amide;
K_D.Nal_D.Cpa.YW_DKTFT(ε-K)GCD.amide;
K_DK.Nal_D.Cpa.YW_DKTFT(ε-K)GCDD.amide;
K_DKK.Nal_D.Cpa.YW_DKTFT(ε-K)GCDDD.amide;
K_DKK.Nal_D.Cpa.YW_DKTFT(ε-K)GCDD.amide;
K_DKKK.Nal_D.Cpa.YW_DKTFT(ε-K)GCDD.amide;
K_DKKK.Nal_D.Cpa.YW_DKTFT(ε-K)GCKDKD.amide;
K_DKKKF_D.Cpa.YW_DKFT.Nal.(ε-K)GCDDDD.amide;
K(BAT).Nal_D.C_{Me}YW_DKVC_{Me}T.amide
K_DDKD.Nal_D.Cpa.YW_DKTFT(ε-K)GCKDKD.amide;
KDKD.Nal_D.CPa.YW_DKTFT(ε-K)GCKDKD.amide;
F_D.Cpa.YW_DKTC(ε-K)GCKK.amide;
F_D.Cpa.YW_DKTC(ε-K)GC.amide;
F_D.Cpa.YW_DKTFT(ε-K)GCKK.amide;
F_D.Cpa.YW_DK.Abu.Nal.T(ε-K)GC.amide;
F_D.Cpa.YW_DKTFTGGG(ε-K)GC.amide;
F_D.Cpa.YW_DKTFT(ε-K)GCR.amide;
(Trc-imide).Nal_D.Cpa.YW_DKTFT(ε-K)GCR.amide;
Trc.(Trc-imide).K.Nal_D.Cpa.YW_DKTFT(ε-K)GCRR.amide;
(Trc-imide)_2K.Nal_D.Cpa.YW_DKTFT(ε-K)GCRR.amide;
(Trc-imide)_2K.Nal_D.Cpa.YW_DKTFT(ε-K)GCR.amide;
D_DDF_D.Cpa.YW_DKTFT(ε-K)GCKK.amide;
D_DF_D.Cpa.YW_DKTFT(ε-K)GCKK.amide;
F_DFYW_DKTFT(ε-K)GCKK.amide;
AKCGGGF_DYW_DKTFT.amide;
(2-ketogulonyl).Nal_D.CPa.YW_DKTFT(ε-K)GCKK.amide;
(2-ketogulonyl).F_D.Cpa.YW_DKTFT(ε-K)GC.amide;
cyclo-(N—CH_3)FYW_DKV.Hcy(CH_2CO.GC.Dap.Dap.amide);
cyclo-(N—CH_3)FYW_DKV.Hcy(CH_2CO.(γ-Dab)KCR.amide);
cyclo-(N—CH_3)FYW_DKV.Hcy(CH_2CO.KKKKK(ε-K)GC.amide);
cyclo-(N—CH_3)FYW_DKV.Hcy(CH_2CO).(ε-K)GCK.amide;
cyclo-(N—CH_3)FYW_DKV.Hcy(CH_2CO.(β-Dap)KCR.amide);
cyclo-(N—CH_3)FYW_DKV.Hcy(CH_2CO.(β-Dap)KCK.amide);
cyclo-(N—CH_3)FYW_DKV.Hcy(CH_2CO.(δ-Orn)GCK.amide);
cyclo-(N—CH_3)FYW_DKV.Hcy(CH_2CO.(β-Dap)GCK.amide);
cyclo-(N—CH_3)FYW_DKV.Hcy(CH_2CO.K(ε-K)KCK.amide);
cyclo-(N—CH_3)FYW_DKV.Hcy(CH_2CO.(ε-K)GCKK.amide);
cyclo-(N—CH_3)FYW_DKV.Hcy(CH_2CO).K(ε-K)GC.amide;
cyclo-(N—CH_3)FYW_DKV.Hcy(CH_2CO).(ε-K)GC.amide;
RGCQAPLYKKIIKKLLES (SEQ ID NO:8);
acetyl.KK(ε-K)GCGCGGPLYKKIIKKLLES (SEQ ID NO:14);
acetyl.KXKXKK(ε-K)GCGGPLYKKIIKKLLES (SEQ ID NO:15);
(CH_2CO.Y_D.Amp.GDCKGCG.amide)_2(CH_2CO)_2K(ε-K)GC.amide;
(CH_2CO.Y_D.Amp.GDCGGC_{Acm}GC_{Acm}GGC.amide)_2(CH_2CO)_2K(ε-K)GC.amide;
(CH_2CO.Y_D.ApcGDCKGCG.amide)_2(CH_2CO)_2K(ε-K)GC.amide;
{(CH_2CO.Y_D.ApcGDCGGCG.amide)(CH_2CO)}_2K(ε-K)GC.amide;
(CH_2CO.Y_D.ApcGDCKGG)_2K(ε-K)GC.β-Ala.amide;
(CH_2CO.Y_D.ApcGDCKKG)_2K(ε-K)GC.β-Ala.amide;
{(CH_2CO.Y_D.ApcGDCG)_2KG}_2K(ε-K)GCG.amide;
(CH_2CO.Y_D.ApcGDC)_2K(ε-K)GCG.amide;
({(CH_2CO.Y_D.ApcGDCGGC_{Acm}GC_{Acm}GGC.amide)(CH_2CO)}_2.K)_2K(ε-K)GCG.amide;
{(CH_2CO.Y_D.ApcGDCGGC_{Acm}GC_{Acm}GGC.amide)_2(CH_2CO)_2K}_2K(ε-K)GCG.amide;
(CH_2CO.Y_D.ApcGDCGGC_{Acm}GC_{Acm}GGC.amide)_2(CH_2CO)_2K(ε-K)GC.amide;
HSDAVFTDNYTRLRKQMAVKKYLNSILN(ε-K)GC.amide (SEQ ID NO:16);
HSDAVFTDNYTRLRKQMAVKKYLNSILNGGC.amide (SEQ ID NO:9);
AGCHSDAVFTDNYTRLRKQMAVKKYLNSILN.amide (SEQ ID NO:10);
HSDAVFTDNYTRLRKQMAVKKYLNSILNC(BAT).amide (SEQ ID NO:11);
CH_2CO.SNLST.HhcVLGKLSC(BAT)ELHKLQTYPRTNTGSGTP.amide (SEQ ID NO:12);
CH_2CO.SNLST.HhcVLGKLSQELHKLQTYPRTNTGSGTP(ε-K)GC.amide (SEQ ID NO:17);
CH_2CO.SNLST.HhcVLGKLSC(CH_2CO.GGCK.amide)ELHKLQTYPRTNTGSGTP.amide (SEQ ID NO:18);
CH_2CO.SNLST.HhcVLGKLSC(CH_2CO.(β-Dap)KCK.amide)ELHKLQTYPRTNTGSGTP.amide (SEQ ID NO:19);
CH_2CO.SNLST.HhcVLGKLSC(CH_2CO.(ε-K)GCE.amide)ELHKLQTYPRTNTGSGTP.amide (SEQ ID NO:20);
CH_2CO.SNLST.HcyVLGKLSC(CH_2CO.GGGK.amide)ELHKLQTYPRTNTGSGTP.amide (SEQ ID NO:21);
CH_2CO.SNLST.HcyVLGKLSC(CH_2CO.(β-Dap)KCK.amide)ELHKLQTYPRTNTGSGTP.amide (SEQ ID NO:22);
CH_2CO.SNLST.HcyVLGKLSC(CH_2CO.(ε-K)GCE.amide)ELHKLQTYPRTNTGSGTP.amide (SEQ ID NO:23);
CH_2CO.SNLST.CysLGKLSC(CH_2CO.GGCK.amide)ELHKLQTYPRTNTGSGTP.amide (SEQ ID NO:24);
CH_2CO.SNLST.CysVLGKLSC(CH_2CO.(β-Dap)KCK.amide)ELHKLQTYPRTNTGSGTP.amide (SEQ ID NO:25);
CH_2CO.SNLST.CysVLGKLSC(CH_2CO.(ε-K)GCE.amide)ELHKLQTYPRTNTGSGTP.amide (SEQ ID NO:26);
SNLST.AsuVLGKLSC(CH_2CO.(β-Dap)KCK.amide)ELHKLQTYPRTNTGSGTP.amide (SEQ ID NO:27),
SNLST.AsuVLGKLSC(CH_2CO.(β-Dap)KCK.amide)ELHKLQTYPRTNTGSGTP.amide (SEQ ID NO:28);
cyclo-Tyr-D-Trp-Lys-Thr-Phe-(N—CH_3)Hcy(CH_2CO-β-Dap-Tyr-Cys-Thr(ol));

cyclo-Tyr-D-Trp-Lys-Thr-Phe-(N—CH₃)Hcy(CH₂CO-β-Dap-Phe(4-F)-Cys-Thr(ol));
cyclo-Tyr-D-Trp-Lys-Thr-Phe-(N—CH₃)Hcy(CH₂CO-β-Dap- Phe(4-NH₂)-Cys-Thr-Ser);
cyclo-Tyr-D-Trp-Lys-Thr-Phe-(N—CH₃)Hcy(CH₂CO-β-Dap- Dab-Cys-Thr);
cyclo-Tyr-D-Trp-Lys-Thr-Phe-(N—CH₃)Hcy(CH₂CO-β-Dap- Phe(4-NH₂)-Cys-Thr);
cyclo-Tyr-D-Trp-Lys-Thr-Phe-(N—CH₃)Hcy(CH₂CO-β-Dap- Phe(4-NH₂)-Cys-Thr(ol));
cyclo-Tyr-D-Trp-Lys-Thr-Phe-(N—CH₃)Hcy(CH₂CO-β-Dap- His-Cys-Thr(ol));
cyclo-Tyr-D-Trp-Lys-Thr-Phe-(N—CH₃)Hcy(CH₂CO-β-Dap- Arg-Cys-Thr(ol));
cyclo-Tyr-D-Trp-Lys-Thr-Phe-(N—CH₃)Hcy(CH₂CO-β-Dap- Gly-Cys-Lys-NH₂);
cyclo-Tyr-D-Trp-Lys-Thr-Phe-(N—CH₃)Hcy(CH₂CO-β-Dap- Ser-Cys-Thr(ol));
cyclo-Tyr-D-Trp-Lys-Thr-Phe-(N—CH₃)Hcy(CH₂CO-β-Dap- Dab-Cys-Thr(ol));
cyclo-Tyr-D-Trp-Lys-Thr-Phe-(N—CH₃)Hcy(CH₂CO-β-Dap- Gly-Cys-Thr(ol));
cyclo-Tyr-D-Trp-Lys-Thr-Phe-(N—CH₃)Hcy(CH₂CO-β-Dap- Dab-Cys-Ser(ol));
cyclo-Tyr-D-Trp-Lys-Thr-Phe-(N—CH₃)Hcy(CH₂CO-Gly-Gly- Cys-Lys-NH₂);
cyclo-Tyr-D-Trp-Lys-Thr-Phe-(N—CH₃)Hcy(CH₂CO-Gly-Gly- Cys-Arg-NH₂);
cyclo-Tyr-D-Trp-Lys-Thr-Phe-(N—CH₃)Hcy(CH₂CO-Ser-Ser- Cys-Lys-NH₂);
cyclo-Tyr-D-Trp-Lys-Thr-Phe-(N—CH₃)Hcy(CH₂CO-Ser-Ser- Cys-Arg-NH₂);
cyclo-Tyr-D-Trp-Lys-Thr-Phe-(N—CH₃)Hcy(CH₂CO-Ser-Ser- Cys-Lys-Thr(ol));
cyclo-Tyr-D-Trp-Lys-Thr-Phe-(N—CH₃)Hcy(CH₂CO-Ser-Ser- Cys-Dap-NH₂);
cyclo-Tyr-D-Trp-Lys-Thr-Phe-(N—CH₃)Hcy(CH₂CO-Ser-Ser- Cys-NH(CH₂CH₂O) ₂CH₂CH₂NH₂);
cyclo-Tyr-D-Trp-Lys-Thr-Phe-(N—CH₃)Hcy(CH₂CO-β-Dap- Ser-Cys-Thr-NH(CH₂CH₂O) ₂CH₂CH₂NH₂);
cyclo-Tyr-D-Trp-Lys-Thr-Phe-(N—CH₃)Hcy(CH₂CO-Gly-Lys- Cys-NH₂);
cyclo-Tyr-D-Trp-Lys-Thr-Phe-(N—CH₃)Hcy(CH₂CO-Ser-Lys- Cys-NH₂);
cyclo-Tyr-D-Trp-Lys-Thr-Phe-(N—CH₃)Hcy(CH₂CO-Lys-Gly- Cys-NH₂);
cyclo-Tyr-D-Trp-Lys-Thr-Phe-(N—CH₃)Hcy(CH₂CO-Ser-Dab- Cys-Ser(ol));
cyclo-Tyr-D-Trp-Lys-Thr-Phe-(N—CH₃)Hcy(CH₂CO-Ser-Dap- Cys-NH₂);
cyclo-Tyr-D-Trp-Lys-Thr-Phe-(N—CH₃)Hcy(CH₂CO-Gly-Gly- Cys-His-NH₂);
cyclo-Tyr-D-Trp-Lys-Thr-Phe-(N—CH₃)Hcy(CH₂CO-Gly-Gly- Cys-Phe(4-NH₂)—NH₂);
cyclo-Tyr-D-Trp-Lys-Thr-Phe-(N—CH₃)Hcy(CH₂CO-β-Dap- Orn-Cys-Thr(ol));
cyclo-Tyr-D-Trp-Lys-Thr-Phe-(N—CH₃)Hcy(CH₂CO-β-Dap- Dap-Cys-Thr(ol));
cyclo-Tyr-D-Trp-Lys-Thr-Phe-(N—CH₃)Hcy(CH₂CO-β-Dap- Lys-Cys-Thr(ol));
cyclo-Tyr-D-Trp-Lys-Thr-Phe-(N—CH₃)Hcy(CH₂CO-Ser-Ser- Cys-NHCH₂CH₂OCH₂CH₂NH₂);
cyclo-Tyr-D-Trp-Lys-Thr-Phe-(N—CH₃)Hcy(CH₂CO-β-Dap- Lys-Cys-NH₂);
cyclo-Tyr-D-Trp-Lys-Thr-Phe-(N—CH₃)Hcy(CH₂CO-δ-Orn- Gly-Cys-NH₂); and
cyclo-Tyr-D-Trp-Lys-Thr-Phe-(N—CH₃)Hcy(CH₂CO-Thr-Gly- Gly-Cys-NH₂).

(Single-letter and three-letter abbreviations for amino acids can be found in G. Zubay, *Biochemistry* (2d. ed.), 1988 (MacMillan Publishing: New York) p.33; other abbreviations are as follows: Acm is acetamidomethyl; Mob is 4-methoxybenzyl; Abu is aminobutyric acid; $F_D$ is D-phenylalanine; $W_D$ is D-tryptophan; $Y_D$ is D-tyrosine; Aca is 6-aminohexanoic acid; Apc is S-(3-aminopropyl) cysteine; Hcv is homocyseine; Nal is 2-naphthylalanine; Cpa is 4-chlorophenylalanine; $K_D$ is D-lysine; $D_D$ is D-aspartate; $Nal_D$ is D-2-naphthylalanine; DTPA is diethylenetriaminepentaacetic acid; Trc is tricarballylic acid; Trc-imide is tricarballylic imide; and Hca is hexacarboxycyclohexane. ( ... )₂K represents covalent linkage to both amino groups of lysine. Hcy( ... ) represents covalent linkage to the sidechain sulfur atom of homocysteine. (N—CH₃)F represents N-α-methyl-phenylalanine. Underlining between groups (e.g., as between the CH₂CO. group and cysteine (C) in CH₂CO.Y_DRGDC) represents a cyclic sulfide. Underlining between amino acids (e.g., as between the cysteines (C) in CNPRGDC(SEQ ID NO:29)) represents a cyclic disulfide bond. The term "cyclo" before an underlined sequence means an N-terminus-to-C-terminus cyclic sequence. The subscript $X_D$ indicates the amino acid is in the D-configuration; all other subscripts refer to amino acid sidechain protecting groups. ε-K, δ-Orn, γ-Dab, and β-Dap are defined as set forth above. Asu is 2-amino suberic acid, wherein the amino terminal amino acids of peptides containing an Asu residue are cyclized via an amide bond between the amino terminal amino group and the side chain carboxylic acid moiety of the Asu residue. BAT is $N^6$, $N^9$-bis(2-mercapto-2-methylpropyl)-6,9-diazanonanoic acid.

In addition, a hydrophilic thioether may be used in accordance with the present invention to stabilize labelled radiopharmaceutical precursors comprising a targeting moiety or domain covalently linked to the known chelators 1,4,7,10-tetraazadodecanetetraacetic acid and derivatives thereof:

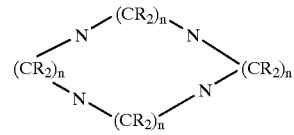

where n is an integer that is 2 or 3 and where each R is independently H, $C_1$ to $C_4$ alkyl, or aryl and one R is covalently linked to the targeting moiety, and desferrioxamine.

A radiopharmaceutical comprising any radionuclide or radiometal may be stabilized in accordance with the present invention. For example, radiopharmaceuticals containing such nuclides as $^{125}$I, $^{131}$I, $^{211}$At, $^{47}$Sc, $^{67}$Cu, $^{72}$Ga, $^{90}$Y, $^{153}$Sm, $^{159}$Gd, $^{165}$Dy, $^{166}$Ho, $^{175}$Yb, $^{177}$Lu, $^{186}$Re, $^{188}$Re, $^{212}$Bi, $^{213}$Bi, $^{68}$Ga, $^{99m}$Tc, $^{111}$In, and $^{123}$I, and the like may be stabilized by addition of a hydrophilic thioether in accordance with the invention. The extent of stabilization of a particular radiopharmaceutical precursor when chelated to different radionuclides may vary. For example, a $^{99m}$Tc-labelled precursor may be stabilized to a greater extent than a $^{188}$Re-labelled form of the same precursor.

The compositions of the invention are formulated as a sterile, pyrogen-free, parenterally acceptable aqueous solution which may optionally be supplied in lyophilized form and be reconstituted by the user. The compositions of the invention may be provided as components of kits which may include buffers, additional vials, instructions for use, and the like.

The pharmaceutical compositions of the invention comprises a radiopharmaceutical precursor in combination with a stabilizing amount of a hydrophilic thioether, optionally with a pharmaceutically acceptable diluent or a carrier such as species appropriate albumin. As used herein, a "pharmaceutically acceptable diluent or carrier" may include any and all solvents, dispersion media, antibacterial and antifungal agents, isotonic agents, enzyme inhibitors, transfer ligands such as glucoheptonate, tartrate, citrate, or mannitol, and the like. The use of such media and agents for pharmaceutically active substances is well known in the art. For example, Sodium Chloride Injection and Ringer's Injection are commonly used as diluents. The preparation of such parenterally acceptable solutions, having due regard to pH, isotonicity, stability, and the like, is within the skill in the art.

In accordance with the method of this invention, radiopharmaceuticals are preferably administered intravenously in a single unit dose, either totally as a bolus or partly as a bolus followed by infusion over 1–2 hours. The amount of solution to be injected at unit dosage is from about 0.01 mL to about 10 mL, containing about 0.01 mCi to about 100 mCi of radioactivity, preferably from about 1 mCi to about 50 mCi. The amount of the radiopharmaceutical in the unit dose may range from about 0.1 to about 10 mg/kg body weight, After intravenous administration, the site is monitored, for example, by radioimaging in vivo if the radiopharmaceutical is a diagnostic agent.

The following examples are shown by way of illustration and not be considered as limitations.

EXAMPLE 1

Effect of Gentisic Acid on Radiochemical Purity of $^{99m}$Tc-labelled Depreotide Gentisic acid (GA) was tested for its ability to stabilize the $^{99m}$Tc-labelled somatostatin receptor-binding peptide depreotide, which has the structure.

This peptide is represented as:
cyclo(
N—CH$_3$)FYW$_D$KV.Hcy.(CH$_2$CO.(β-Dap)KCK.amide)
in the listing set forth above.

Lyophilized kit vials were prepared containing depreotide, GA, and other components as described in Table 1. Formulations were adjusted to pH 7.4 or 8.5 (as noted) prior to lyophilization.

TABLE 1

| Component | Control | GA I | GA II | GA III |
|---|---|---|---|---|
| Depreotide | 50 μg | 50 μg | 50 μg | 50 μg |
| Sodium Glucoheptonate Dihydrate[1] | 25 mg | 25 mg | 5 mg | 25 mg |
| Edetate Disodium Dihydrate[2] | 100 μg | 100 μg | 100 μg | 100 μg |
| Stannous Chloride Dihydrate[3] | 50 μg | 50 μg | 50 μg | 50 μg |
| Gentisic Acid Sodium Salt Hydrate[4] | — | 1 mg | 1 mg | 1 mg |
| pH | 7.4 | 7.4 | 7.4 | 8.5 |

[1]Pfanstiehl Laboratories, Waukegan, Illinois, USA.
[2]J. T. Baker, Phillipsburg, New Jersey, USA.
[3]Acros Organics/Fisher Scientific, Pittsburgh, Pennsylvania, USA.
[4]Sigma Chemical Co., St. Louis, Missouri, USA.

The lyophilized kits were radiolabelled with $^{99m}$Tc by reconstitution with 1.0 mL technetium $^{99m}$Tc sodium pertechnetate (Technelite® Molybdenum Mo99-Technetium Tc99m Generator, DuPont, Billerica, Mass.) containing approximately 50 mCi $^{99m}$Tc and heating in a boiling water bath for 10 minutes. Radiolabelling yield (RCP) results as measured by reversed phase HPLC are given in Table 2.

TABLE 2

| | HPLC RCP (%) | | |
|---|---|---|---|
| Formulation | 0.5 hr | 3.5 hr | 6.5 hr |
| Control | 94.5 | 88.3 | 86.4 |
| | 94.2 | 92.1 | 90.8 |
| | 94.5 | 91.7 | 90.1 |
| (Average ± 1SD): | (94.4 ± 0.2) | (90.7 ± 2.1) | (89.1 ± 2.4) |
| GA I | 82.4 | 79.4 | 77.2 |
| GA II | 29.1 | 25.1 | 20.5 |
| GA III | 0.9 | 0.7 | 0.6 |

These results indicate that gentisic acid decreases the radiolabelling yield and the stability of $^{99m}$Tc-depreotide when included in formulated kits.

EXAMPLE 2

Stabilization of $^{99m}$Tc-labelled Depreotide by L-Methionine

Lyophilized kit vials were prepared containing depreotide, L-methionine (Met), and other components as

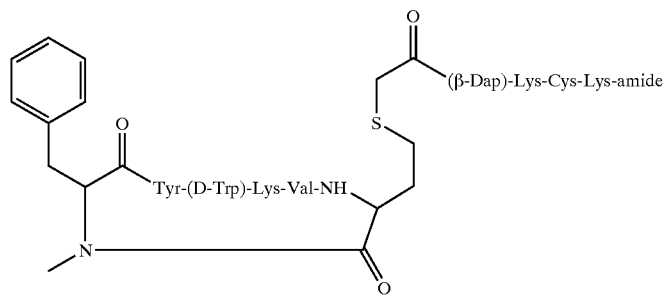

described in Table 3. All formulations were adjusted to pH 7.4 prior to lyophilization.

TABLE 3

| Component | Control | Met I | Met II | Met III | Met IV | Met V |
|---|---|---|---|---|---|---|
| Depreotide | 50 μg | 50 μg | 50 μg | 50 μg | 50 μg | 50 μg |
| Sodium Glucoheptonate Dihydrate | 5 mg | 5 mg | 5 mg | 5 mg | 5 mg | 5 mg |
| Edetate Disodium Dihydrate | 100 μg | 100 μg | 100 μg | 100 μg | 100 μg | 100 μg |
| Stannous Chloride Dihydrate | 50 μg | 50 μg | 50 μg | 50 μg | 50 μg | 50 μg |
| L-Methionine USP[1] | — | 1 mg | 2 mg | 4 mg | 5 mg | 10 mg |

[1]Sigma Chemical Co., St. Louis, Missouri, USA.

The lyophilized kits were radiolabelled with $^{99m}$Tc by reconstitution with 1.0 mL technetium $^{99m}$Tc sodium pertechnetate (Technelite®) containing approximately 50 mCi $^{99m}$Tc and heating in a boiling water bath for 10 minutes. Some of the formulations were also radiolabelled in a room temperature preparation (allowed to stand at room temperature 30 minutes following reconstitution). Radiolabelling yield (RCP) results as measured by reversed phase HPLC are given in Table 4.

TABLE 4

| | | HPLC RCP (%) | | |
|---|---|---|---|---|
| Formulation | Prep Type | 0.5 hr | 3.5 hr | 6.5 hr |
| Control | Heated | 91.9 | 85.0 | 80.7 |
|  | Heated | — | 81.6 | 79.3 |
| (Average): |  | (91.9) | (83.3) | (80.0) |
|  | Rm Temp | 94.8 | 87.6 | 78.2 |
|  | Rm Temp | 90.7 | 88.7 | 83.4 |
| (Average): |  | (92.8) | (88.2) | (80.8) |
| Met I (1 mg) | Heated | 95.9 | 91.5 | 89.5 |
| Met II (2 mg) | Heated | 95.2 | 93.2 | 90.5 |
| Met III (4 mg) | Heated | 95.9 | 93.5 | 92.2 |
|  | Heated | 92.4 | 88.5 | 87.4 |
| (Average): |  | (94.2) | (91.0) | (89.8) |
|  | Rm Temp | 90.4 | 90.0 | 89.4 |
|  | Rm Temp | 89.9 | 89.9 | 89.7 |
|  | Rm Temp | 91.4 | 87.9 | 83.1 |
| (Average ± 1SD): |  | (90.6 ± 0.8) | (89.3 ± 1.2) | (87.4 ± 3.7) |
| Met IV (5 mg) | Heated | 93.8 | 93.7 | 93.5 |
|  | Heated | — | 92.5 | 92.7 |
| (Average): |  | (93.8) | (93.1) | (93.1) |
| Met V (10 mg) | Heated | 94.5 | 94.6 | 92.6 |

These results indicate that L-methionine increases the radiolabelling yield and the stability of $^{99m}$Tc-depreotide prepared from formulated kits which have been stored under normal conditions (≤−10° C.).

EXAMPLE 3

Stabilization of $^{99m}$Tc-labelled Depreotide by L-Methionine in Lyophilized Kit Preparations; Accelerated Temperature (40° C.) Storage Lyophilized kits were prepared containing depreotide, L-methionine (Met), and other components as described in Table 5. All formulations were adjusted to pH 7.4 prior to lyophilization. The kits were stored for one week at 40° C. Some kits were also stored at −10° C. as controls.

TABLE 5

| Component | Control | Met |
|---|---|---|
| Depreotide | 50 μg | 50 μg |
| Sodium Glucoheptonate Dihydrate | 5 mg | 5 mg |
| Edetate Disodium Dihydrate | 100 μg | 100 μg |
| Stannous Chloride Dihydrate | 50 μg | 50 μg |
| L-Methionine USP | — | 5 mg |

The lyophilized kits were radiolabelled with $^{99m}$Tc by reconstitution with 1.0 mL technetium $^{99m}$Tc sodium pertechnetate (Technelite ) containing approximately 50 mCi $^{99m}$Tc and incubation in a boiling water bath (10 min). Radiolabelling yield (RCP) results as measured by reversed phase HPLC are given in Table 6.

TABLE 6

| | | | HPLC RCP (%) | | |
|---|---|---|---|---|---|
| Formulation | Storage Temp | Prep Type | 0.5 hr | 3.5 hr | 6.5 hr |
| Control | −10° C. | Heated | — | 82.6 | 77.8 |
|  | 40° C. | Heated | — | 82.6 | 79.0 |
| Met | 40° C. | Heated | 76.5 | 78.0 | 77.6 |

These results indicate that L-methionine does not stabilize $^{99m}$Tc-depreotide in lyophilized kits which have been stored at 40° C. prior to radiolabelling.

EXAMPLE 4

Stabilization of $^{99m}$Tc-labelled Benzodiazepinedione Derivative by L-Methionine in Lyophilized Kit Preparations L-methionine was tested for its ability to stabilize a $^{99m}$Tc-labelled glycoprotein IIb/IIIa receptor-binding benzodiazepinedione derivative 1-[(carboxyglycyl-glycyl-glycyl-cysteinamide)methyl]-4-(2-carboxyethyl)-7-[(4-amidinophenyl)methyl]-3,4-dihydro-1H-1,4-benzodiazepine-2,5-dione trifluoroacetate, having the structure.

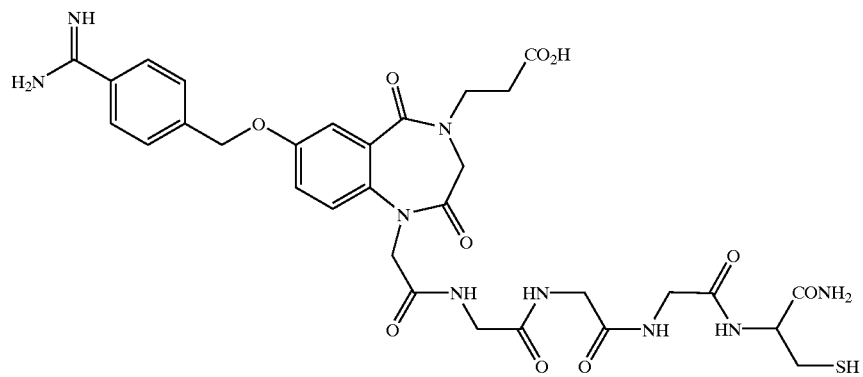

Lyophilized kit vials were prepared containing the benzodiazepinedione derivative and components as described in Table 7. All formulations were adjusted to pH 7.4 prior to lyophilization.

TABLE 7

| Component | Control | Met |
| --- | --- | --- |
| Derivative | 40 μg | 40 μg |
| Sodium Glucoheptonate Dihydrate | 25 mg | 25 mg |
| Edetate Disodium Dihydrate | 100 μg | 100 μg |
| Stannous Chloride Dihydrate | 50 μg | 50 μg |
| L-Methionine USP | — | 5 mg |

The lyophilized kits were radiolabelled with $^{99m}$Tc by reconstitution with 1.0 mL technetium $^{99m}$Tc sodium pertechnetate (Technelite®) containing approximately 50 mCi $^{99m}$Tc and heating in a boiling water bath for 10 minutes. Radiolabelling yield (RCP) results as measured by reversed phase HPLC are given in Table 8.

TABLE 8

| | HPLC RCP (%) | | |
| --- | --- | --- | --- |
| Formulation | 0.5 hr | 3.5 hr | 6.5 hr |
| Control | 93.2 | 90.1 | 88.0 |
| | 93.6 | 94.5 | 88.8 |
| | 92.4 | 89.2 | 88.1 |
| | 85.0 | 86.1 | 82.3 |
| (Average ± 1SD): | (91.0 ± 4.1) | (90.0 ± 3.5) | (86.8 ± 3.0) |
| Met (5 mg) | 92.5 | 91.1 | 91.4 |
| | 93.9 | 92.5 | 91.9 |
| | 94.3 | 92.4 | 91.0 |
| | 90.5 | 91.2 | 91.9 |
| (Average ± 1SD): | (92.8 ± 1.7) | (91.8 ± 0.8) | (91.6 ± 0.4) |

These results indicate that L-methionine increases the radiolabelling yield and the stability of the $^{99m}$Tc-labelled benzodiazepinedione derivative prepared from formulated kits.

EXAMPLE 5

Stabilization of Tc 99m-labelled Peptide by L-Methionine

L-methionine was tested for its ability to stabilize a $^{99m}$Tc-labelled glycoprotein IIb/IIIa receptor-binding peptide having the structure.

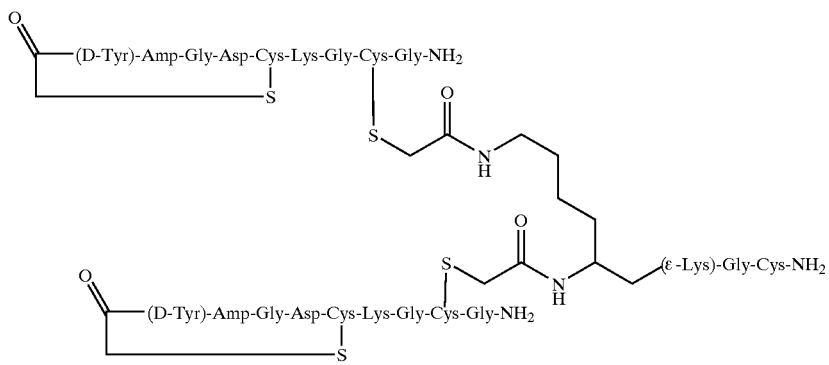

This peptide is represented as:
(CH$_2$CO.Y$_D$.Amp.GDC.KGCG.amide)$_2$(CH$_2$CO)$_2$K (ε-K)GC.amide
in the listing set forth above.

Lyophilized kit vials were prepared containing the peptide (50 μg), sodium glucoheptonate dihydrate (10 mg), stannous chloride dihydrate (50 μg), and edetate disodium dihydrate (100 μg). The formulation was adjusted to pH 7.4 prior to lyophilization.

The lyophilized kits were radiolabelled with $^{99m}$Tc in the presence and absence of L-methionine. To the Met preparation was added 4 mg methionine (in 100 μL saline) and 100 μL ethanol. To the control preparation was added 100 μL ethanol and 100 μL saline to account for the additional saline or ethanol added with the L-methionine. Both vials were then reconstituted with 1.0 mL technetium $^{99m}$Tc sodium pertechnetate (Technelite®) containing approximately 50 mCi $^{99m}$Tc and allowed to incubate for 30 minutes at room temperature. Radiolabelling yield (RCP) results as measured by reversed phase HPLC are given in Table 9.

TABLE 9

| Preparation | HPLC RCP (%) | | |
|---|---|---|---|
| | 0.5 hr | 3.5 hr | 6.5 hr |
| Control | 91.8 | 80.4 | 76.2 |
| Methionine (4 mg) | 96.7 | 96.9 | 96.2 |

These results show that L-methionine increases the radiolabelling yield and the stability of the $^{99m}$Tc-peptide.

EXAMPLE 6

Stabilization of $^{99m}$Tc-labelled Peptide Chelator by L-Methionine

L-methionine was tested for its ability to stabilize a $^{99m}$Tc-labelled monoamine, diamide, single thiol peptide chelator having the structure.

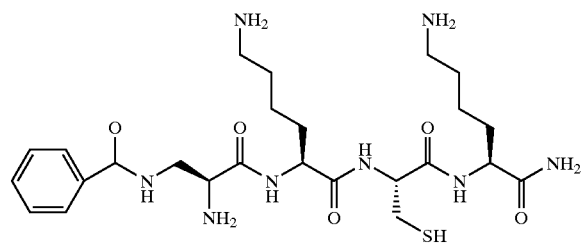

N-3-benzoyl-2,3-(S)-diaminopropionyl-L-lysinyl-L-cysteinyl-L-lysinyl amide

Lyophilized kit "placebo" vials were prepared containing sodium glucoheptonate dihydrate, edetate disodium dihydrate, and stannous chloride dihydrate at the concentrations set forth in Table 1 (control formulation).

The peptide chelator was radiolabelled with $^{99m}$Tc in the presence and absence of L-methionine. The peptide chelator was dissolved in water at a concentration of 1 mg/mL, and 50 μg (50 μL) of the peptide was added to each of three placebo vials. Ethanol and L-methionine were added to the control and methionine preparations as described in Example 5. In addition, 100 μL phosphate buffered saline (PBS) was added to each preparation. The vials were reconstituted with 0.9–1.0 mL $^{99m}$Tc sodium pertechnetate (Technelite®) containing approximately 50 mCi $^{99m}$Tc, and heated in a boiling water bath for ten minutes. Radiolabelling yield (RCP) results as measured by reversed phase HPLC are given in Table 10.

TABLE 10

| Preparation | HPLC RCP (%) | | | |
|---|---|---|---|---|
| | 0.5 hr | 3 hr | 6 hr | 9 hr |
| Control | 94.1 | 92.4 | 85.9 | 80.0 |
| L-Methionine (4 mg) | 98.4 | 97.2 | 95.5 | 92.8 |

These results show that L-methionine increases the radiolabelling yield and the stability of a $^{99m}$Tc-labelled peptide chelator.

EXAMPLE 7

Stabilization of a $^{99m}$Tc Bisamine Bisthiol Chelator by L-Methionine

L-methionine was tested for its ability to stabilize a $^{99m}$Tc-labelled non-peptide chelator (4-(butanoic acid)-2,2,9,9tetramethyl-4,7-diaza-1,10-decanedithiol) having the structure.

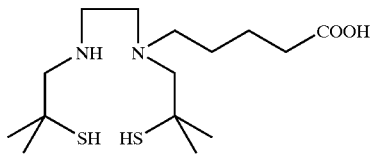

The non-peptide chelator was radiolabelled with $^{99m}$Tc in the presence and absence of L-methionine using the placebo vial heated preparation procedure as described in Example 6. Radiolabelling yield (RCP) results as measured by reversed phase HPLC are given in Table 11.

TABLE 11

| Preparation | HPLC RCP (%) | | | |
|---|---|---|---|---|
| | 0.5 hr | 3 hr | 6 hr | 9 hr |
| Control | 48.5 | 56.5 | 54.0 | 52.9 |
| Methionine (4 mg) | 66.7 | 70.0 | 70.8 | 70.4 |

These results show that L-methionine increases the radiolabelling yield and the stability of a $^{99m}$Tc-labelled non-peptide chelator.

EXAMPLE 8

Stabilization of a $^{99m}$Tc-labelled Peptide by Methionine Derivatives 2-(Ethylthio)ethylamine, methioninol, and 3-methylthio-1,2-propanediol are hydrophilic thioethers having the structures.

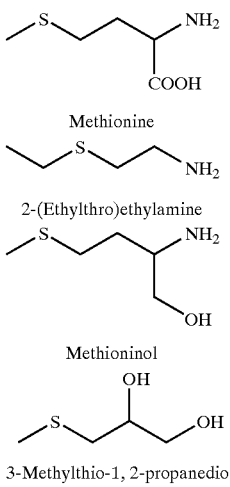

These compounds and L-methionine were tested for their ability to stabilize $^{99m}$Tc-labelled depreotide.

Each hydrophilic thioether was dissolved in water made up at 40 mg/mL and adjusted to pH 7 with HCl or NaOH.

Each hydrophilic thioether (4 mg in 100 μL) was added to a formulated kit vial containing the peptide ("control" formulation in Table 1). To the control vials were added 100 μL water. The vials were reconstituted with 1.0 mL $^{99m}$Tc sodium pertechnetate (Technelite®) containing approximately 50 mCi $^{99m}$Tc and heated in a boiling water bath for ten minutes. Radiolabelling yield (RCP) results as measured by reversed phase HPLC are given in Table 12.

TABLE 12

| Additive | Initial RCP | 3.5 hr RCP | 6.5 hr RCP |
|---|---|---|---|
| Day 1: | | | |
| None (Control 1) | 89.8 | 82.9 | 79.4 |
| Methionine | 95.0 | 90.4 | 89.3 |
| 2-(Ethylthio)ethylamine | 92.8 | 94.2 | 93.3 |
| Day 2: | | | |
| None (Control 2) | 89.9 | 78.0 | 74.4 |

TABLE 12-continued

| Additive | Initial RCP | 3.5 hr RCP | 6.5 hr RCP |
|---|---|---|---|
| Methioninol | 94.1 | 93.9 | 90.7 |
| 3-Methylthio-1,2-propanediol | 89.1 | 84.0 | 80.9 |

These results show that the hydrophilic thioethers 2-(ethylthio)ethylamine, methioninol, and 3-methylthio-1,2-propanediol increase the radiolabelling yield and the stability of a $^{99m}$Tc-labelled peptide. Methionine sulfoxide, methionine sulfone, and 3-(methylthio)propionaldehyde had no effect on $^{99m}$Tc-labelled peptide radiolabelling yield or stability.

It should be understood that the foregoing disclosure emphasizes certain specific embodiments of the invention and that all modifications or equivalents thereto are within the spirit and scope of the invention as set forth in the appended claims.

What is claimed is:

1. A composition comprising: (1) a radiopharmaceutical precursor comprising a chelator optionally covalently linked to a targeting domain or a targeting moiety selected from the group consisting of an antibody, a Fab antibody fragment, a F(ab)'$_2$ antibody fragment, an epitone binding complementarity determining region derived from an antibody, a peptide, a growth factor, a receptor binding fragment of a growth factor, a hormone, a steroid, a receptor binding nuecleic acid, a receptor binding monosaccharide, a receptor binding disaccharide, a receptor binding oligosaccharide, a receptor-binding lipid, and a recertor binding antibiotic; and (2) a stabilizing amount of a hydrophilic thioether of the formula $$R—S—CH_2C(R^1R^2R^3)$$

wherein:

R is $C_1$ to $C_4$ alkyl or a $C_1$ to $C_4$ alkyl containing at least one hydrophilic group selected from —COOH, —NH$_2$, —NHR$^4$, —NR$^4_2$, —OH, —SO$_2$R$^4$, —SOR$^4$, —SO$_3$H, —CONH$_2$, —CONHR$^4$, —CONR$^4_2$, —COOR$^4$, —OR$^4$, —SR$^4$, —NO$_2$, —SO$_2$NH$_2$, —SO$_2$NHR$^4$, and —SO$_2$NR$^4_2$; with the proviso that, when R is methyl, the hydrophilic group is not —NH$_2$, NHR$^4$, NR$^4_2$ or OH;

R$^1$, R$^2$, and R$^3$ are each independently selected from the group consisting of —H, —COOH, —NH$_2$, —NHR$^4$, —NR$^4_2$, —OH, —SO$_2$R$^4$, —SOR$^4$, —SO$_3$H, —CONH$_2$, —CONHR$^4$, —CONR$^4_2$, —COOR$^4$, —OR$^4$, —SR$^4$, —NO$_2$, —SO$_2$NH$_2$, —SO$_2$NHR$^4$, —SO$_2$NR$^4_2$, $C_1$ to $C_4$ alkyl, and a $C_1$ to $C_3$ alkyl containing at least one hydrophilic group selected from —COOH, —NH$_2$, —NHR$^4$, —NR$^4_2$, —OH, —SO$_2$, —SO$_3$R$^4$, —SO$_3$H, —CONH$_2$, —CONHR$^4$, —CONR$^4_2$, —COOR$^4$, —OR$^4$, —SR$^4$, —NO$_2$, —SO$_2$NH$_2$, —SO$_2$NHR$^4$, and —SO$_2$NR$^4_2$, with the proviso that only one of R$^1$, R$^2$, and R$^3$ is —NH$_2$, —NHR$^4$, —NR$^4_2$ or —OH; and R$^4$ is selected from the group consisting of $C_1$ to $C_3$ alkyl; and with the further proviso that the hydrophilic thioether comprise at least one of said hydrophilic groups.

2. The composition of claim 1, wherein the thioether is selected from the group consisting of D-methionine, L-methionine, 3-(methylthio)propionaldehyde, D-ethionine, L-ethionine, 3-methylthio-1,2-propanediol, methyl-3-(methylthio)propionate, 2-(ethylthio)ethylamine, 2-(methylthio)-ethanol, buthionine, S-methyl-L-cysteine, S-methyl-D-cysteine, D-methioninol, and L-methioninol.

3. The composition of claim 2, wherein the thioether is selected from the group consisting of D-methionine, L-methionine, 2-(ethylthio)ethylamine, D-methioninol, L-methioninol, and 3-methylthio-1,2-propanediol.

4. The composition of claim 3, wherein the thioether is L-methionine.

5. The composition of claim 1, wherein the precursor comprises a targeting moiety selected from the group consisting of an antibody, a Fab antibody fragment, a F(ab)'$_2$ antibody fragment, an epitope binding complementarity determining region derived from an antibody, a peptide, a growth factor, a receptor binding fragment of a growth factor, a hormone, a steroid, a receptor binding nucleic acid, a receptor binding monosaccharide, a receptor binding disaccharide, a receptor binding oligosaccharide, a receptor-binding lipid, and a receptor binding antibiotic.

6. The composition of claim 5, wherein the targeting moiety is a peptide.

7. The composition of claim 1, wherein the precursor comprises a peptide chelator.

8. The composition of claim 1, wherein the precursor comprises a non-peptide chelator.

9. The composition of claim 1, further comprising a radionuclide.

10. The composition of claim 9, wherein the radionuclide is selected from the group consisting of $^{125}$I, $^{131}$I, $^{211}$At, $^{47}$Sc, $^{67}$Cu, $^{72}$Ga, $^{90}$Y, $^{153}$Sm, $^{159}$Gd, $^{165}$Dy, $^{166}$Ho, $^{175}$Yb, $^{177}$Lu, $^{212}$Bi, $^{213}$Bi, $^{68}$Ga, $^{99m}$Tc, $^{111}$In, and $^{123}$I.

11. A composition according to claim 6, wherein the targeting moiety is selected from the group consisting of:

GGCSIPPEVKFNKPFVYLIamide (SEQ ID NO:1);

GGCSIPPEVKFNKPFVYLI (SEQ ID NO:2);

GGCGLF (SEQ ID NO:3);

RGCSIPPEVKFNKPFVYLI.amide (SEQ ID NO:4);

RGCGHRPLDKKREEAPSLRPAPPISGGYR.amide (SEQ ID NO:5);

GGCRPKPQQFFGLM.amide (SEQ ID NO:6);

GGCFVYLI.amide (SEQ ID NO:7);

(acetyl.TKPRGG)$_2$K(ε-K)GC.amide (SEQ ID NO:13);

F$_D$FYW$_D$KTFT(ε-K)GC.amide;

acetyl.F$_D$FYW$_D$KTFT(ε-K)GC.amide;

acetyl.Nal.$_D$.Cpa.YW$_D$KTFT(ε-K)GCKK.amide;

acetyl.F$_D$FYW$_D$KTFTGGG(ε-K)GC.amide;

acetyl.F$_D$FYW$_D$KTFTGGG(ε-K)KC.amide;

acetyl.KKKKK.Nal$_D$.Cpa.YW$_D$KTFT(ε-K)GC.amide;

acetyl.D$_D$F$_D$.Cpa.YW$_D$KTFT(ε-K)GCKK.amide;

acetyl.D$_D$F$_D$.Cpa.YW$_D$KTC(ε-K)GCKK.amide;

acetyl.KKKKK.Nal$_D$.Cpa.YW$_D$KTFT(ε-K)GCKK.amide;

acetyl.Nal$_D$.Cpa.YW$_D$KTFT($\epsilon$-K)GCKK.amide;
acetyl.DDD.Nal$_D$.Cpa.YW$_D$KTFT($\epsilon$-K)GCKK.amide;
acetyl.D$_D$DF$_D$.Cpa.YW$_D$KTFT($\epsilon$-K)GCKK.amide;
(DTPA).F$_D$FYW$_D$KTFT($\epsilon$-K)GC.amide;
(DTPA).Nal$_D$.Cpa.YW$_D$KT.Nal.T($\epsilon$-K)GCKK.amide;
(DTPA).($\epsilon$-K)GCF$_D$FYW$_D$KTFT.amide;
(DTPA).($\epsilon$-K)GCF$_D$.Cpa.YW$_D$KTFT.amide;
(DTPA).F$_D$.Cpa.YW$_D$KTFT($\epsilon$-K)GC.amide;
(DTPA).Nal$_D$.Cpa.YW$_D$KTFT($\epsilon$-K)GC.amide;
(DTPA).Aca.F$_D$.Cpa.YW$_D$KTFT($\epsilon$-K)GC.amide;
(DTPA).Nal$_D$.Cpa.YW$_D$KT.Nal.T($\epsilon$-K)GCKK.amide;
(DTPA).Nal$_D$.Cpa.YW$_D$KTFT($\epsilon$-K)GCKK.amide;
CH$_2$CO.FFW$_D$KTFC($\epsilon$-K)GC.amide;
CH$_2$CO.FFW$_D$KTFCKKKKK($\epsilon$-K)GC.amide;
CH$_2$CO.FFW$_D$KTFC($\epsilon$-K)KKKKKGC.amide;
AKCGGGF$_D$FYW$_D$KTFT.amide;
AKCGGGF$_D$YW$_D$KTFT.amide;
DDDD.Nal$_D$.Cpa.YW$_D$KTFT($\epsilon$-K)GCKKKK.amide;
DDD.Nal$_D$.Cpa.YW$_D$KTFT($\epsilon$-K)GCKK.amide;
Nal$_D$.Cpa.YW$_D$KTFT($\epsilon$-K)GCKK.amide;
Trc.Nal$_D$.Cpa.YW$_D$KTFT($\epsilon$-K)GCKK.amide;
Hca.Nal$_D$.Cpa.YW$_D$KTFT($\epsilon$-K)GCKK.amide;
(Trc)$_2$.Nal$_D$.Cpa.YW$_D$KTFT($\epsilon$-K)GCKK.amide;
KKKKK.Nal$_D$.Cpa.YW$_D$KTFT($\epsilon$-K)GCDDDD.amide;
K$_D$.Nal$_D$.Cpa.YW$_D$KTFT($\epsilon$-K)GCD.amide;
K$_D$K.Nal$_D$.Cpa.YW$_D$KTFT($\epsilon$-K)GCDD.amide;
K$_D$KK.Nal$_D$.Cpa.YW$_D$KTFT($\epsilon$-K)GCDDD.amide;
K$_D$KK.Nal$_D$.Cpa.YW$_D$KTFT($\epsilon$-K)GCDD.amide;
K$_D$KKK.Nal$_D$.Cpa.YW$_D$KTFT($\epsilon$-K)GCDD.amide;
K$_D$KKK.Nal$_D$.Cpa.YW$_D$KTFT($\epsilon$-K)GCKDKD.amide;
K$_D$KKK.F$_D$.Cpa.YW$_D$KTF,Nal.($\epsilon$-K)GCDDDD.amide;
K(BAT).Nal$_D$.C$_{Me}$YW$_D$KVC$_{Me}$T.amide
K$_D$DKD.Nal$_D$.Cpa.YW$_D$KTFT($\epsilon$-K)GCKDKD.amide;
KDKD.Nal$_D$.Cpa.YW$_D$KTFT($\epsilon$-K)GCKDKD.amide;
F$_D$.Cpa.YW$_D$KTC($\epsilon$-K)GCKK.amide;
F$_D$.Cpa.YW$_D$KTC($\epsilon$-K)GC.amide;
F$_D$.Cpa.YW$_D$KTFT($\epsilon$-K)GCKK.amide;
F$_D$.Cpa.YW$_D$.Abu.Nal.T($\epsilon$-K)GC.amide;
F$_D$.Cpa.YW$_D$KTFTGGG($\epsilon$-K)GC.amide;
F$_D$.Cpa.YW$_D$KTFT($\epsilon$-K)GCR.amide;
(Trc-imide).Nal$_D$.Cpa.YW$_D$KTFT($\epsilon$-K)GCR.amide;
Trc.(Trc-imide).K.Nal$_D$.Cpa.YW$_D$KTFT($\epsilon$-K) GCRR.amide;
(Trc-imide)$_2$.K.Nal$_D$.Cpa.YW$_D$KTFT($\epsilon$-K)GCRR.amide;
(Trc-imide)$_2$.K.Nal$_D$.Cpa.YW$_D$KTFT($\epsilon$-K)GCR.amide;
D$_D$DF$_D$.Cpa.YW$_D$KTFT($\epsilon$-K)GCKK.amide;
D$_D$F$_D$.Cpa.YW$_D$KTFT($\epsilon$-K)GCKK.amide;
F$_D$FYW$_D$KTFT($\epsilon$-K)GCKK.amide;
AKCGGGF$_D$YW$_D$KTFT.amide;
(2-ketogulonyl).Nal$_D$.Cpa.YW$_D$KTFT($\epsilon$-K) GCKK.amide;
(2-ketogulonyl).F$_D$.Cpa.YW$_D$KTFT($\epsilon$-K)GC.amide;
cyclo-(N—CH$_3$)FYW$_D$KV.Hcy(CH$_2$CO.GC.Dap.Dap. amide);
cyclo-(N—CH$_3$)FYW$_D$KV.Hcy(CH$_2$CO.($\gamma$-Dab)KCR. amide);
cyclo-(N—CH$_3$)FYW$_D$KV.Hcy(CH$_2$CO.KKKKK($\epsilon$-K) GC.amide);
cyclo-(N—CH$_3$)FYW$_D$KV.Hcy(CH$_2$CO).($\epsilon$-K)GCK. amide;
cyclo-(N—CH$_3$)FYW$_D$KV.Hcy(CH$_2$CO.($\beta$-Dap)KCR. amide);
cyclo-(N—CH$_3$)FYW$_D$KV.Hcy(CH$_2$CO.($\delta$-Dap)KCK. amide);
cyclo-(N—CH$_3$)FYW$_D$KV.Hcy(CH$_2$CO.($\delta$-Orn)GCK. amide);
cyclo-(N—CH$_3$)FYW$_D$KV.Hcy(CH$_2$CO.($\beta$-Dap)GCK. amide);
cyclo-(N—CH$_3$)FYW$_D$KV.Hcy(CH$_2$CO.K($\epsilon$-K)KCK. amide);
cyclo-(N—CH$_3$)FYW$_D$KV.Hcy(CH$_2$CO.($\epsilon$-K)GCKK. amide);
cyclo-(N—CH$_3$)FYW$_D$KV.Hcy(CH$_2$CO.($\epsilon$-K)GC.amide;
cyclo-(N—CH$_3$)FYW$_D$KV.Hcy(CH$_2$CO.($\epsilon$-K)GC. amide);
RGCQAPLYKKIIKKLLES (SEQ ID NO:8);
acetyl.KK($\epsilon$-K)GCGCGGPLYKKIIKKLLES (SEQ ID NO:14);
acetyl.KKKKKK($\epsilon$-K)GCGGPLYKKIIKKLLES (SEQ ID NO:15);
(CH$_2$CO.Y$_D$.Amp.GDCKGCG.amide)$_2$(CH$_2$CO)$_2$K($\epsilon$-K) GC.amide;
(CH$_2$CO.Y$_D$.Amp.GDCGGC$_{Acm}$GC$_{Acm}$GGC.amide)$_2$ (CH$_2$CO)$_2$K($\epsilon$-K)GC.amide;
(CH$_2$CO.Y$_D$.Apc.GDCKGCG.amide)$_2$(CH$_2$CO)$_2$K($\epsilon$-K) GC.amide;
{(CH$_2$CO.Y$_D$.Apc.GDCGGCG.amide)(CH$_2$CO)}$_2$K ($\epsilon$-K)GC.amide;
(CH$_2$CO.Y$_D$.Apc.GDCKGG)$_2$K($\epsilon$-K)GC.$\beta$-Ala.amide;
(CH$_2$CO.Y$_D$.Apc.GDCKKG)$_2$K($\epsilon$-K)GC.$\beta$-Ala.amide;
{(CH$_2$CO.Y$_D$.Apc.GDCG)$_2$KG)}$_2$K($\epsilon$-K)GCG.amide;
(CH$_2$CO.Y$_D$.Apc.GDC$_2$K($\epsilon$-K)GCG.amide;
({(CH$_2$CO.Y$_D$.Apc.GDCGGC$_{Acm}$GC$_{Acm}$GGC.amide) (CH$_2$CO)}$_2$.K)$_2$K($\epsilon$-K)GCG.amide;
{(CH$_2$CO.Y$_D$.Apc.GDCGGC$_{Acm}$GC$_{Acm}$GGC.amide)$_2$ (CH$_2$CO)$_2$K}$_2$)K($\epsilon$-K)GCG.amide;
(CH$_2$CO.Y$_D$.Apc.GDCGGC$_{Acm}$GC$_{Acm}$GGC.amide)$_2$ (CH$_2$CO)$_2$K($\epsilon$-K)GC.amide;
HSDAVFTDNYTRLRKQMAVKKYLNSILN($\epsilon$-K) GC.amide (SEQ ID NO:16);
HSDAVFTDNYTRLRKQMAVKKYLNSIL-NGGC.amide (SEQ ID NO:9);
AGCHSDAVFTDNYTRLRKQMAVKKYLN-SILN.amide (SEQ ID NO:10);
HSDAVFTDNYTRLRKQMAVKKYLNSILNC(BAT). amide (SEQ ID NO:11);
CH$_2$CO.SNLST.HhcVLGKLSC(BAT)ELHKLQTYP RTNTGSGTP.amide (SEQ ID NO:12);
CH$_2$CO.SNLST.HhcVLGKLSQELHKLQTYPRTNTGS GTP($\epsilon$-K)GC.amide (SEQ ID NO:17);
CH$_2$CO.SNLST.HhcVLGKLSC(CH$_2$CO.GGCK.amide) ELHKLQTYPRTNTGSGTP.amide (SEQ ID NO:18);
CH$_2$CO.SNLST.HhcVLGKLSC(CH$_2$CO.($\beta$-Dap)KCK. amide)ELHKLQTYPRTNTGSGTP.amide (SEQ ID NO: 19);
CH$_2$CO.SNLST.HhcVLGKLSC(CH$_2$CO.($\epsilon$-K)GCE. amide)ELHKLQTYPRTNTGSGTP.amide (SEQ ID NO:20);
CH$_2$CO.SNLST.HcyVLGKLSC(CH$_2$CO.GGCK.amide) ELHKLQTYPRTNTGSGTP.amide (SEQ ID NO:21);

CH₂CO.SNLST.HcyVLGKLSC(CH₂CO.(β-Dap)KCK.
  amide)ELHKLQTYPRTNTGSGTP.amide (SEQ ID NO:22);
CH₂CO.SNLST.HcyVLGKLSC(CH₂CO.(ε-K)GCE.
  amide)ELHKLQTYPRTNTGSGTP.amide (SEQ ID NO:23);
CH₂CO.SNLST.CysLGKLSC(CH₂CO.GGCK.amide)
  ELHKLQTYPRTNTGSGTP.amide (SEQ ID NO:24);
CH₂CO.SNLST.CysVLGKLSC(CH₂CO.(β-Dap)KCK.
  amide)ELHKLQTYPRTNTGSGTP.amide (SEQ ID NO:25);
CH₂CO.SNLST.CysVLGKLSC(CH₂CO.(ε-K)GCE.
  amide)ELHKLQTYPRTNTGSGTP.amide (SEQ ID NO:26);
SNLST.AsuVLGKLSC(CH₂CO.(β-Dap)KCK.amide)
  ELHKLQTYPRTNTGSGTP.amide (SEQ ID NO:27);
SNLST.AsuVLGKLSC(CH₂CO.(β-Dap)KCK.amide)
  ELHKLQTYPRTNTGSGTP.amide (SEQ ID NO:28);
cyclo-Tyr-D-Trp-Lys-Thr-Phe-(N—CH₃)Hcy(CH₂CO-β-
  ap-Tyr-Cys-Thr(ol));
cyclo-Tyr-D-Trp-Lys-Thr-Phe-(N—CH₃)Hcy(CH₂CO-β-
  Dap-Phe(4-F)-Cys-Thr(ol));
cyclo-Tyr-D-Trp-Lys-Thr-Phe-(N—CH₃)Hcy(CH₂CO-β-
  Dap-Phe(4-NH₂)-Cys-Thr-Ser);
cyclo-Tyr-D-Trp-Lys-Thr-Phe-(N—CH₃)Hcy(CH₂CO-β-
  Dap-Dab-Cys-Thr);
cyclo-Tyr-D-Trp-Lys-Thr-Phe-(N—CH₃)Hcy(CH₂CO-β-
  Dap-Phe-(4-NH₂)-Cys-Thr);
cyclo-Tyr-D-Trp-Lys-Thr-Phe-(N—CH₃)Hcy(CH₂CO-β-
  Dap-Phe(4-NH₂)-Cys-Thr(ol));
cyclo-Tyr-D-Trp-Lys-Thr-Phe-(N—CH₃)Hcy(CH₂CO-β-
  Dap-His-Cys-Thr(ol));
cyclo-Tyr-D-Trp-Lys-Thr-Phe-(N—CH₃)Hcy(CH₂CO-β-
  Dap-Arg-Cys-Thr(ol));
cyclo-Tyr-D-Trp-Lys-Thr-Phe-(N—CH₃)Hcy(CH₂CO-β-
  Dap-Gly-Cys-Lys-NH₂);
cyclo-Tyr-D-Trp-Lys-Thr-Phe-(N—CH₃)Hcy(CH₂CO-β-
  Dap-Ser-Cys-Thr(ol));
cyclo-Tyr-D-Trp-Lys-Thr-Phe-(N—CH₃)Hcy(CH₂CO-β-
  Dap-Dab-Cys-Thr(ol));
cyclo-Tyr-D-Trp-Lys-Thr-Phe-(N—CH₃)Hcy(CH₂CO-β-
  Dap-Gly-Cys-Thr(ol));
cyclo-Tyr-D-Trp-Lys-Thr-Phe-(N—CH₃)Hcy(CH₂CO-β-
  Dap-Dap-Cys-Ser(ol));
cyclo-Tyr-D-Trp-Lys-Thr-Phe-(N—CH₃)Hcy(CH₂CO-
  Gly-Gly-Cys-Lys-NH₂);
cyclo-Tyr-D-Trp-Lys-Thr-Phe-(N—CH₃)Hcy(CH₂CO-
  Gly-Gly-Cys-Arg-NH₂);
cyclo-Tyr-D-Trp-Lys-Thr-Phe-(N—CH₃)Hcy(CH₂CO-
  Ser-Ser-Cys-Lys-NH₂);
cyclo-Tyr-D-Trp-Lys-Thr-Phe-(N—CH₃)Hcy(CH₂CO-
  Ser-Ser-Cys-Arg-NH₂);
cyclo-Tyr-D-Trp-Lys-Thr-Phe-(N—CH₃)Hcy(CH₂CO-
  Ser-Ser-Cys-Lys-Thr(ol));
cyclo-Tyr-D-Trp-Lys-Thr-Phe-(N—CH₃)Hcy(CH₂CO-
  Ser-Ser-Cys-Dap-NH₂);
cyclo-Tyr-D-Trp-Lys-Thr-Phe-(N—CH₃)Hcy(CH₂CO-
  Ser-Ser-Cys-NH(CH₂CH₂O)₂CH₂CH₂NH₂);
cyclo-Tyr-D-Trp-Lys-Thr-Phe-(N—CH₃)Hcy(CH₂CO-β-
  Dap- Ser-Cys-Thr-NH(CH₂CH₂O)₂CH₂CH₂NH₂);
cyclo-Tyr-D-Trp-Lys-Thr-Phe-(N—CH₃)Hcy(CH₂CO-
  Gly-Lys-Cys-NH₂);
cyclo-Tyr-D-Trp-Lys-Thr-Phe-(N—CH₃)Hcy(CH₂CO-
  Ser-Lys-Cys-NH₂);
cyclo-Tyr-D-Trp-Lys-Thr-Phe-(N—CH₃)Hcy(CH₂CO-
  Lys-Gly-Cys-NH₂);
cyclo-Tyr-D-Trp-Lys-Thr-Phe-(N—CH₃)Hcy(CH₂CO-
  Ser-Dab-Cys-Ser(ol));
cyclo-Tyr-D-Trp-Lys-Thr-Phe-(N—CH₃)Hcy(CH₂CO-
  Ser-Dap-Cys-NH₂);
cyclo-Tyr-D-Trp-Lys-Thr-Phe-(N—CH₃)Hcy(CH₂CO-
  Gly-Gly-Cys-His-NH₂);
cyclo-Tyr-D-Trp-Lys-Thr-Phe-(N—CH₃)Hcy(CH₂CO-
  Gly-Gly-Cys-Phe(4-NH₂)-NH₂);
cyclo-Tyr-D-Trp-Lys-Thr-Phe-(N—CH₃)Hcy(CH₂CO-β-
  Dap-Orn-Cys-Thr(ol));
cyclo-Tyr-D-Trp-Lys-Thr-Phe-(N—CH₃)Hcy(CH₂CO-β-
  Dap-Dap-Cys-Thr(ol));
cyclo-Tyr-D-Trp-Lys-Thr-Phe-(N—CH₃)Hcy(CH₂CO-β-
  Dap-Lys-Cys-Thr(ol));
cyclo-Tyr-D-Trp-Lys-Thr-Phe-(N—CH₃)Hcy(CH₂CO-
  Ser-Ser-Cys-NHCH₂CH₂OCH₂CH₂NH₂);
cyclo-Tyr-D-Trp-Lys-Thr-Phe-(N—CH₃)Hcy(CH₂CO-β-
  Dap-Lys-Cys-NH₂);
cyclo-Tyr-D-Trp-Lys-Thr-Phe-(N—CH₃)Hcy(CH₂CO-δ-
  Orn-Gly-Cys-NH₂); and
cyclo-Tyr-D-Trp-Lys-Thr-Phe-(N—CH₃)Hcy(CH₂CO-
  Thr-Gly-Cys-Cys-NH₂).

12. The composition of claim 11, wherein said thioether is methionine.

13. The composition of claim 12, wherein the peptide is cyclo-(N—CH₃)FYW_DKV.Hcy(CH₂CO.(β-Dap)KCK.amide).

14. The composition of claim 12, wherein the peptide is cyclo-Tyr-D-Trp-Lys-Thr-Phe-(N—CH₃)Hcy(CH₂CO-β-Dap-Phe(4-NH₂-Cys-Thr-Ser).

15. The composition of any of claims 11 through 14, further comprising a radionuclide.

16. The composition of claim 15, wherein the radionuclide is $^{99m}$Tc.

17. A method of stabilizing a radiopharmaceutical comprising the steps of:
  a) combining a radiopharmaceutical precursor according to claim 1 with a stabilizing amount of a hydrophilic thioether according to claim 1 in a container; and
  b) adding a radionuclide to the container.

18. The method of claim 17, wherein the thioether is methionine.

19. The method of claims 17 or 18, wherein the radionuclide is $^{99m}$Tc.

20. A kit comprising a sealed vial containing a predetermined quantity of a radiopharmaceutical precursor according to claim 1 and a stabilizing amount of a hydrophilic thioether according to claim 1.

21. The kit of claim 20, wherein the thioether is methionine.

22. The kit of claim 21, wherein the precursor is cyclo-(N—CH₃)FYW_DKV.Hcy(CH₂CO.(β-Dap)KCK.amide).

23. The kit of claim 21, wherein the precursor is cyclo-Tyr-D-Trp-Lys-Thr-Phe-(N—CH₃)Hcy(CH₂CO-β-Dap-Phe-(4-NH₂)-Cys-Thr-Ser).

* * * * *

SEQUENCE LISTING

```
<160> NUMBER OF SEQ ID NOS: 29

<210> SEQ ID NO 1
<211> LENGTH: 19
<212> TYPE: PRT
<213> ORGANISM: Artificial Sequence
<220> FEATURE:
<223> OTHER INFORMATION: Synthetic construct
<220> FEATURE:
<221> NAME/KEY: AMIDATION
<222> LOCATION: 19

<400> SEQUENCE: 1

Gly Gly Cys Ser Ile Pro Pro Glu Val Lys Phe Asn Lys Pro Phe Val
1               5                   10                  15

Tyr Leu Ile

<210> SEQ ID NO 2
<211> LENGTH: 19
<212> TYPE: PRT
<213> ORGANISM: Artificial Sequence
<220> FEATURE:
<223> OTHER INFORMATION: Synthetic construct

<400> SEQUENCE: 2

Gly Gly Cys Ser Ile Pro Pro Glu Val Lys Phe Asn Lys Pro Phe Val
1               5                   10                  15

Tyr Leu Ile

<210> SEQ ID NO 3
<211> LENGTH: 6
<212> TYPE: PRT
<213> ORGANISM: Artificial Sequence
<220> FEATURE:
<223> OTHER INFORMATION: Synthetic construct

<400> SEQUENCE: 3

Gly Gly Cys Gly Leu Phe
1               5
```

```
<210> SEQ ID NO 4
<211> LENGTH: 19
<212> TYPE: PRT
<213> ORGANISM: Artificial Sequence
<220> FEATURE:
<223> OTHER INFORMATION: Synthetic construct
<220> FEATURE:
<221> NAME/KEY: AMIDATION
<222> LOCATION: 19

<400> SEQUENCE: 4
```

Arg Gly Cys Ser Ile Pro Pro Glu Val Lys Phe Asn Lys Pro Phe Val
 1               5                  10                  15

Tyr Leu Ile

```
<210> SEQ ID NO 5
<211> LENGTH: 30
<212> TYPE: PRT
<213> ORGANISM: Artificial Sequence
<220> FEATURE:
<223> OTHER INFORMATION: Synthetic construct
<220> FEATURE:
<221> NAME/KEY: AMIDATION
<222> LOCATION: 30

<400> SEQUENCE: 5
```

Arg Gly Cys Gly His Arg Pro Leu Asp Lys Lys Arg Glu Glu Ala Pro
 1               5                  10                  15

Ser Leu Arg Pro Ala Pro Pro Pro Ile Ser Gly Gly Tyr Arg
            20                  25                  30

```
<210> SEQ ID NO 6
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: AMIDATION
<222> LOCATION: 14

<400> SEQUENCE: 6
```

Gly Gly Cys Arg Pro Lys Pro Gln Gln Phe Phe Gly Leu Met
 1               5                  10

```
<210> SEQ ID NO 7
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: AMIDATION
<222> LOCATION: 8

<400> SEQUENCE: 7
```

Gly Gly Cys Phe Val Tyr Leu Ile
 1               5

```
<210> SEQ ID NO 8
<211> LENGTH: 18
<212> TYPE: PRT
<213> ORGANISM: Artificial Sequence
<220> FEATURE:
<223> OTHER INFORMATION: Synthetic construct

<400> SEQUENCE: 8
```

```
Arg Gly Cys Gln Ala Pro Leu Tyr Lys Ile Ile Lys Lys Leu Leu
 1               5                  10                  15

Glu Ser

<210> SEQ ID NO 9
<211> LENGTH: 31
<212> TYPE: PRT
<213> ORGANISM: Artificial Sequence
<220> FEATURE:
<223> OTHER INFORMATION: Synthetic construct
<220> FEATURE:
<221> NAME/KEY: AMIDATION
<222> LOCATION: 31

<400> SEQUENCE: 9

His Ser Asp Ala Val Phe Thr Asp Asn Tyr Thr Arg Leu Arg Lys Gln
 1               5                  10                  15

Met Ala Val Lys Lys Tyr Leu Asn Ser Ile Leu Asn Gly Gly Cys
            20                  25                  30

<210> SEQ ID NO 10
<211> LENGTH: 31
<212> TYPE: PRT
<213> ORGANISM: Artificial Sequence
<220> FEATURE:
<223> OTHER INFORMATION: Synthetic construct
<220> FEATURE:
<221> NAME/KEY: AMIDATION
<222> LOCATION: 31

<400> SEQUENCE: 10

Ala Gly Cys His Ser Asp Ala Val Phe Thr Asp Asn Tyr Thr Arg Leu
 1               5                  10                  15

Arg Lys Gln Met Ala Val Lys Lys Tyr Leu Asn Ser Ile Leu Asn
            20                  25                  30

<210> SEQ ID NO 11
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 29
<223> OTHER INFORMATION: BAT: N6, N9 - bis (mercapto-2-methylpropyl)-6,
      9-diazanonanoic acid
<220> FEATURE:
<221> NAME/KEY: AMIDATION
<222> LOCATION: 29

<400> SEQUENCE: 11

His Ser Asp Ala Val Phe Thr Asp Asn Tyr Thr Arg Leu Arg Lys Gln
 1               5                  10                  15

Met Ala Val Lys Lys Tyr Leu Asn Ser Ile Leu Asn Cys
            20                  25

<210> SEQ ID NO 12
<211> LENGTH: 31
<212> TYPE: PRT
<213> ORGANISM: Artificial Sequence
<220> FEATURE:
<223> OTHER INFORMATION: Synthetic construct
<220> FEATURE:
<221> NAME/KEY: ACETYLATION
<222> LOCATION: 1
<220> FEATURE:
<221> NAME/KEY: VARIANT
```

```
<222> LOCATION: 6
<223> OTHER INFORMATION: Xaa = Hhc: Homohomocysteine
<220> FEATURE:
<221> NAME/KEY: VARIANT
<222> LOCATION: 13
<223> OTHER INFORMATION: BAT: N6,N9-bis (mercapto-2-methylpropyl)-6,
      9-diazanonanoic acid
<220> FEATURE:
<221> NAME/KEY: AMIDATION
<222> LOCATION: 31

<400> SEQUENCE: 12

Ser Asn Leu Ser Thr Xaa Val Leu Gly Lys Leu Ser Cys Glu Leu His
1               5                   10                  15

Lys Leu Gln Thr Tyr Pro Arg Thr Asn Thr Gly Ser Gly Thr Pro
            20                  25                  30

<210> SEQ ID NO 13
<211> LENGTH: 16
<212> TYPE: PRT
<213> ORGANISM: Artificial Sequence
<220> FEATURE:
<223> OTHER INFORMATION: Synthetic construct
<220> FEATURE:
<221> NAME/KEY: ACETYLATION
<222> LOCATION: 1
<220> FEATURE:
<221> NAME/KEY: VARIANT
<222> LOCATION: 14
<223> OTHER INFORMATION: Xaa = epsilon-Lysine
<220> FEATURE:
<221> NAME/KEY: AMIDATION
<222> LOCATION: 16

<400> SEQUENCE: 13

Thr Lys Pro Arg Gly Gly Thr Lys Pro Arg Gly Gly Lys Xaa Gly Cys
1               5                   10                  15

<210> SEQ ID NO 14
<211> LENGTH: 22
<212> TYPE: PRT
<213> ORGANISM: Artificial Sequence
<220> FEATURE:
<223> OTHER INFORMATION: Synthetic construct
<220> FEATURE:
<221> NAME/KEY: ACETYLATION
<222> LOCATION: 1
<220> FEATURE:
<221> NAME/KEY: VARIANT
<222> LOCATION: 3
<223> OTHER INFORMATION: Xaa = epsilon-Lysine

<400> SEQUENCE: 14

Lys Lys Xaa Gly Cys Gly Cys Gly Gly Pro Leu Tyr Lys Lys Ile Ile
1               5                   10                  15

Lys Lys Leu Leu Glu Ser
            20

<210> SEQ ID NO 15
<211> LENGTH: 24
<212> TYPE: PRT
<213> ORGANISM: Artificial Sequence
<220> FEATURE:
<223> OTHER INFORMATION: Synthetic construct
<220> FEATURE:
<221> NAME/KEY: ACETYLATION
<222> LOCATION: 1
<220> FEATURE:
<221> NAME/KEY: VARIANT
<222> LOCATION: 7
<223> OTHER INFORMATION: Xaa = epsilon-Lysine
```

<400> SEQUENCE: 15

Lys Lys Lys Lys Lys Xaa Gly Cys Gly Gly Pro Leu Tyr Lys Lys
1               5                   10                  15

Ile Ile Lys Lys Leu Leu Glu Ser
            20

<210> SEQ ID NO 16
<211> LENGTH: 31
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 29
<223> OTHER INFORMATION: Xaa = epsilon-Lysine
<220> FEATURE:
<221> NAME/KEY: AMIDATION
<222> LOCATION: 31

<400> SEQUENCE: 16

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn Xaa Gly Cys
            20                  25                  30

<210> SEQ ID NO 17
<211> LENGTH: 34
<212> TYPE: PRT
<213> ORGANISM: Artificial Sequence
<220> FEATURE:
<223> OTHER INFORMATION: Synthetic construct
<220> FEATURE:
<221> NAME/KEY: ACETYLATION
<222> LOCATION: 1
<220> FEATURE:
<221> NAME/KEY: VARIANT
<222> LOCATION: 6
<223> OTHER INFORMATION: Xaa = Hhc: Homohomocysteine
<220> FEATURE:
<221> NAME/KEY: VARIANT
<222> LOCATION: 32
<223> OTHER INFORMATION: Xaa = epsilon-Lysine
<220> FEATURE:
<221> NAME/KEY: AMIDATION
<222> LOCATION: 34

<400> SEQUENCE: 17

Ser Asn Leu Ser Thr Xaa Val Leu Gly Lys Leu Ser Gln Glu Leu His
1               5                   10                  15

Lys Leu Gln Thr Tyr Pro Arg Thr Asn Thr Gly Ser Gly Thr Pro Xaa
            20                  25                  30

Gly Cys

<210> SEQ ID NO 18
<211> LENGTH: 35
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 6
<223> OTHER INFORMATION: Xaa = Hhc: Homohomocysteine
<220> FEATURE:
<221> NAME/KEY: ACETYLATION
<222> LOCATION: 1, 14
<220> FEATURE:

```
<221> NAME/KEY: AMIDATION
<222> LOCATION: 17, 35

<400> SEQUENCE: 18

Ser Asn Leu Ser Thr Xaa Val Leu Gly Lys Leu Ser Cys Gly Cys
1               5                   10                  15

Lys Glu Leu His Lys Leu Gln Thr Tyr Pro Arg Thr Asn Thr Gly Ser
            20                  25                  30

Gly Thr Pro
        35

<210> SEQ ID NO 19
<211> LENGTH: 34
<212> TYPE: PRT
<213> ORGANISM: Artificial Sequence
<220> FEATURE:
<223> OTHER INFORMATION: Synthetic construct
<220> FEATURE:
<221> NAME/KEY: ACETYLATION
<222> LOCATION: 1, 14
<220> FEATURE:
<221> NAME/KEY: VARIANT
<222> LOCATION: 14
<223> OTHER INFORMATION: beta-Dap: 2,3 diaminopropionic acid residue
<220> FEATURE:
<221> NAME/KEY: AMIDATION
<222> LOCATION: 16, 34
<220> FEATURE:
<221> NAME/KEY: VARIANT
<222> LOCATION: 6
<223> OTHER INFORMATION: Xaa = Hhc: Homohomocysteine

<400> SEQUENCE: 19

Ser Asn Leu Ser Thr Xaa Val Leu Gly Lys Leu Ser Cys Lys Cys Lys
1               5                   10                  15

Glu Leu His Lys Leu Gln Thr Tyr Pro Arg Thr Asn Thr Gly Ser Gly
            20                  25                  30

Thr Pro

<210> SEQ ID NO 20
<211> LENGTH: 35
<212> TYPE: PRT
<213> ORGANISM: Artificial Sequence
<220> FEATURE:
<223> OTHER INFORMATION: Synthetic construct
<220> FEATURE:
<221> NAME/KEY: ACETYLATION
<222> LOCATION: 1, 14
<220> FEATURE:
<221> NAME/KEY: VARIANT
<222> LOCATION: 6
<223> OTHER INFORMATION: Xaa = Hhc: Homohomocysteine
<220> FEATURE:
<221> NAME/KEY: VARIANT
<222> LOCATION: 14
<223> OTHER INFORMATION: Xaa = epsilon-Lysine
<220> FEATURE:
<221> NAME/KEY: AMIDATION
<222> LOCATION: 17, 35

<400> SEQUENCE: 20

Ser Asn Leu Ser Thr Xaa Val Leu Gly Lys Leu Ser Cys Xaa Gly Cys
1               5                   10                  15

Glu Glu Leu His Lys Leu Gln Thr Tyr Pro Arg Thr Asn Thr Gly Ser
            20                  25                  30

Gly Thr Pro
        35
```

```
<210> SEQ ID NO 21
<211> LENGTH: 35
<212> TYPE: PRT
<213> ORGANISM: Artificial Sequence
<220> FEATURE:
<223> OTHER INFORMATION: Synthetic construct
<220> FEATURE:
<221> NAME/KEY: ACETYLATION
<222> LOCATION: 1, 14
<220> FEATURE:
<221> NAME/KEY: VARIANT
<222> LOCATION: 6
<223> OTHER INFORMATION: Xaa = Hcy: Homocysteine
<220> FEATURE:
<221> NAME/KEY: AMIDATION
<222> LOCATION: 17, 35

<400> SEQUENCE: 21

Ser Asn Leu Ser Thr Xaa Val Leu Gly Lys Leu Ser Cys Gly Gly Cys
 1               5                  10                  15

Lys Glu Leu His Lys Leu Gln Thr Tyr Pro Arg Thr Asn Thr Gly Ser
             20                  25                  30

Gly Thr Pro
         35

<210> SEQ ID NO 22
<211> LENGTH: 34
<212> TYPE: PRT
<213> ORGANISM: Artificial Sequence
<220> FEATURE:
<223> OTHER INFORMATION: Synthetic construct
<220> FEATURE:
<221> NAME/KEY: ACETYLATION
<222> LOCATION: 1, 14
<220> FEATURE:
<221> NAME/KEY: VARIANT
<222> LOCATION: 6
<223> OTHER INFORMATION: Xaa = Hcy: Homocysteine
<220> FEATURE:
<221> NAME/KEY: VARIANT
<222> LOCATION: 14
<223> OTHER INFORMATION: beta-Dap: 2,3 diaminopropionic acid residue
<220> FEATURE:
<221> NAME/KEY: AMIDATION
<222> LOCATION: 16, 34

<400> SEQUENCE: 22

Ser Asn Leu Ser Thr Xaa Val Leu Gly Lys Leu Ser Cys Lys Cys Lys
 1               5                  10                  15

Glu Leu His Lys Leu Gln Thr Tyr Pro Arg Thr Asn Thr Gly Ser Gly
             20                  25                  30

Thr Pro

<210> SEQ ID NO 23
<211> LENGTH: 35
<212> TYPE: PRT
<213> ORGANISM: Artificial Sequence
<220> FEATURE:
<223> OTHER INFORMATION: Synthetic construct
<220> FEATURE:
<221> NAME/KEY: ACETYLATION
<222> LOCATION: 1, 14
<220> FEATURE:
<221> NAME/KEY: VARIANT
<222> LOCATION: 6
<223> OTHER INFORMATION: Xaa = Hcy: Homocysteine
<220> FEATURE:
<221> NAME/KEY: VARIANT
<222> LOCATION: 14
<223> OTHER INFORMATION: Xaa = epsilon-Lysine
```

```
<220> FEATURE:
<221> NAME/KEY: AMIDATION
<222> LOCATION: 17, 35

<400> SEQUENCE: 23

Ser Asn Leu Ser Thr Xaa Val Leu Gly Lys Leu Ser Cys Xaa Gly Cys
 1               5                  10                  15

Glu Glu Leu His Lys Leu Gln Thr Tyr Pro Arg Thr Asn Thr Gly Ser
            20                  25                  30

Gly Thr Pro
        35

<210> SEQ ID NO 24
<211> LENGTH: 35
<212> TYPE: PRT
<213> ORGANISM: Artificial Sequence
<220> FEATURE:
<223> OTHER INFORMATION: Synthetic construct
<220> FEATURE:
<221> NAME/KEY: ACETYLATION
<222> LOCATION: 1, 14
<220> FEATURE:
<221> NAME/KEY: AMIDATION
<222> LOCATION: 17, 35

<400> SEQUENCE: 24

Ser Asn Leu Ser Thr Cys Val Leu Gly Lys Leu Ser Cys Gly Gly Cys
 1               5                  10                  15

Lys Glu Leu His Lys Leu Gln Thr Tyr Pro Arg Thr Asn Thr Gly Ser
            20                  25                  30

Gly Thr Pro
        35

<210> SEQ ID NO 25
<211> LENGTH: 34
<212> TYPE: PRT
<213> ORGANISM: Artificial Sequence
<220> FEATURE:
<223> OTHER INFORMATION: Synthetic construct
<220> FEATURE:
<221> NAME/KEY: ACETYLATION
<222> LOCATION: 1, 14
<220> FEATURE:
<221> NAME/KEY: VARIANT
<222> LOCATION: 14
<223> OTHER INFORMATION: beta-Dap: 2,3 diaminopropionic acid residue
<220> FEATURE:
<221> NAME/KEY: AMIDATION
<222> LOCATION: 16, 34

<400> SEQUENCE: 25

Ser Asn Leu Ser Thr Cys Val Leu Gly Lys Leu Ser Cys Lys Cys Lys
 1               5                  10                  15

Glu Leu His Lys Leu Gln Thr Tyr Pro Arg Thr Asn Thr Gly Ser Gly
            20                  25                  30

Thr Pro

<210> SEQ ID NO 26
<211> LENGTH: 35
<212> TYPE: PRT
<213> ORGANISM: Artificial Sequence
<220> FEATURE:
<223> OTHER INFORMATION: Synthetic construct
<220> FEATURE:
<221> NAME/KEY: ACETYLATION
<222> LOCATION: 1, 14
<220> FEATURE:
```

<221> NAME/KEY: VARIANT
<222> LOCATION: 14
<223> OTHER INFORMATION: Xaa = epsilon-Lysine
<220> FEATURE:
<221> NAME/KEY: AMIDATION
<222> LOCATION: 17, 35

<400> SEQUENCE: 26

Ser Asn Leu Ser Thr Cys Val Leu Gly Lys Leu Ser Cys Xaa Gly Cys
 1               5                  10                  15

Glu Glu Leu His Lys Leu Gln Thr Tyr Pro Arg Thr Asn Thr Gly Ser
             20                  25                  30

Gly Thr Pro
         35

<210> SEQ ID NO 27
<211> LENGTH: 34
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 6
<223> OTHER INFORMATION: Xaa = Asu: 2-amino suberic acid
<220> FEATURE:
<221> NAME/KEY: ACETYLATION
<222> LOCATION: 14
<220> FEATURE:
<221> NAME/KEY: VARIANT
<222> LOCATION: 14
<223> OTHER INFORMATION: beta-Dap: 2,3 diaminopropionic acid residue
<220> FEATURE:
<221> NAME/KEY: AMIDATION
<222> LOCATION: 16, 34

<400> SEQUENCE: 27

Ser Asn Leu Ser Thr Xaa Val Leu Gly Lys Leu Ser Cys Lys Cys Lys
 1               5                  10                  15

Glu Leu His Lys Leu Gln Thr Tyr Pro Arg Thr Asn Thr Gly Ser Gly
             20                  25                  30

Thr Pro

<210> SEQ ID NO 28
<211> LENGTH: 34
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 6
<223> OTHER INFORMATION: Xaa = Asu: 2-amino suberic acid
<220> FEATURE:
<221> NAME/KEY: ACETYLATION
<222> LOCATION: 14
<220> FEATURE:
<221> NAME/KEY: VARIANT
<222> LOCATION: 14
<223> OTHER INFORMATION: beta-Dap: 2,3 diaminopropionic acid residue
<220> FEATURE:
<221> NAME/KEY: AMIDATION
<222> LOCATION: 16, 34

<400> SEQUENCE: 28

Ser Asn Leu Ser Thr Xaa Val Leu Gly Lys Leu Ser Cys Lys Cys Lys
 1               5                  10                  15

Glu Leu His Lys Leu Gln Thr Tyr Pro Arg Thr Asp Val Gly Ala Gly
             20                  25                  30

Thr Pro

<210> SEQ ID NO 29
<211> LENGTH: 7
<212> TYPE: PRT
<213> ORGANISM: Artificial Sequence
<220> FEATURE:
<223> OTHER INFORMATION: Synthetic construct

<400> SEQUENCE: 29

Cys Asn Pro Arg Gly Asp Cys
 1               5